United States Patent
Hsieh et al.

(12)

(10) Patent No.: US 10,383,907 B2
(45) Date of Patent: Aug. 20, 2019

(54) METHOD FOR RELIEVING MEMORY DYSFUNCTION USING PUERARIAE RADIX EXTRACT

(71) Applicant: National Taiwan Normal University, Taipei (TW)

(72) Inventors: Hsiu-Mei Hsieh, Taipei (TW); Hui-Chen Huang, Taipei (TW); Jung-Yaw Lin, Taipei (TW); Ching-Yi Huang, Taoyuan (TW)

(73) Assignee: National Taiwan Normal University, Taipei (TW)

( * ) Notice: Subject to any disclaimer, the term of this patent is extended or adjusted under 35 U.S.C. 154(b) by 145 days.

(21) Appl. No.: 15/676,177

(22) Filed: Aug. 14, 2017

(65) Prior Publication Data
US 2018/0207217 A1    Jul. 26, 2018

(30) Foreign Application Priority Data

Jan. 24, 2017   (TW) ............................. 106102737 A

(51) Int. Cl.
| | |
|---|---|
| *A61K 36/00* | (2006.01) |
| *A61K 36/488* | (2006.01) |
| *A61K 31/7048* | (2006.01) |
| *A61K 31/353* | (2006.01) |
| *A61K 9/00* | (2006.01) |

(52) U.S. Cl.
CPC .......... *A61K 36/488* (2013.01); *A61K 9/0014* (2013.01); *A61K 9/0019* (2013.01); *A61K 9/0053* (2013.01); *A61K 31/353* (2013.01); *A61K 31/7048* (2013.01); *A61K 2236/331* (2013.01)

(58) Field of Classification Search
CPC ..................................................... A61K 36/00
See application file for complete search history.

(56) References Cited

FOREIGN PATENT DOCUMENTS

CN           1969946 A    *   5/2007

* cited by examiner

*Primary Examiner* — Qiuwen Mi
(74) *Attorney, Agent, or Firm* — Wang Law Firm, Inc.

(57) ABSTRACT

A method for relieving memory dysfunction using Puerariae Radix Extract is provided, including decocting Puerariae Radix in water, concentrating the extracted product thereof, and administrating an effective dose of the Puerariae Radix extract to a subject. Since the present invention merely uses Puerariae Radix as an ingredient, it belongs to a Chinese herbal medicine of single drug prescription. Further, with the same amount of Puerarin, Puerariae Radix Extract of the present invention provides a better neuroprotective effect in comparison with Puerarin, which indicates that the Puerariae Radix extract contains more active neurotrophic ingredients other than Puerarin. Therefore, Puerariae Radix extract is more promising potential therapeutic medicine than Puerarin for relieving the symptoms of anxiety and cognitive impairment.

6 Claims, 34 Drawing Sheets
(15 of 34 Drawing Sheet(s) Filed in Color)

METHOD FOR RELIEVING MEMORY DYSFUNCTION USING PUERARIAE RADIX EXTRACT

CROSS-REFERENCE TO RELATED APPLICATION

This application claims priority from Taiwan Patent Application No. 106102737, filed on Jan. 24, 2017, at the Taiwan Intellectual Property Office, the contents of which are hereby incorporated by reference in their entirety for all purposes.

BACKGROUND OF THE INVENTION

1. Field of the Invention

The present invention relates to a method for relieving memory dysfunction using a Puerariae Radix extract. In particular, the present invention relates to a method for relieving memory dysfunction memory dysfunction caused by Alzheimer's disease using a Puerariae Radix Extract.

2. Description of the Related Art

Alzheimer's disease (AD) accounts for 60% to 70% of cases of dementia, and is commonly found in elderly people. Currently, there are about 24 million people around the world suffering from Alzheimer's disease, which increases by 4.6 million cases per year as the aging population increases. The World Health Organization (WHO) has estimated that Alzheimer's will affect 80 million people by the year 2040. Hence, Alzheimer's disease may be one of the most intractable neurodegenerative diseases having high morbidity rate. Alzheimer's disease is a persistent neurological dysfunction which deteriorates over time. Early symptoms of Alzheimer's disease may include amnesia, changing behavior or personality, mild cognitive impairment (MCI), anxiety, and loss of interest in things that had been of interest in past. Symptoms in later stages of Alzheimer's may include delirium, irritability, aggressive behavior, problems with language, disorientation (including easily getting lost), mood swings, loss of motivation, loss of long-term memory, not managing self-care and behavioral issues. Although how the disease progresses varies from person to person, in general, the life expectancy of a confirmed case is three to nine years.

The main pathophysiological features of Alzheimer's disease are 1) β-amyloid (Aβ) fragment accumulation of Aβ-plaques, and 2) hyperphosphorylation of tau protein causing neurofibrillary tangles (NFT), which eventually causes neurons to die. There are a number of possible causes of Alzheimer's disease, including familial Alzheimer's disease (FAD), which accounts for 5% of cases and is caused by gene mutations mainly to one of three genes, those encoding amyloid precursor protein (APP), and presenilins 1 (PS1) and 2 (PS2); and sporadic Alzheimer's disease (SAD), which accounts for most cases and is caused by environmental risk factors such as stress.

The main clinical medicines for Alzheimer's disease include Donepezil, Galantamine, Rivastigmine and Memantine. The first three are mainly used in the early and middle stages of Alzheimer's disease, and act by inhibiting the acetylcholinesterase so as to increase the concentration of acetylcholine, which is the neurotransmitter in the brain. Memantine is an N-methyl-D-aspartate receptor (NMDAR) antagonist and acts by preventing damage to nerve cells from excitotoxicity generated by overactivated NMDAR. However, these treatments only offer minor relief from symptoms and come with side effects such as nausea, slow heartbeat, reduced appetite, weight loss, and increased gastric acid secretion. Many recent studies have used natural or herbal medicines as treatment for Alzheimer's disease that cause less side effects. However, natural medicines for treatment of Alzheimer's disease, such as ginkgo extract, have not worked as well as expected in clinical trials. Therefore, finding a Chinese herbal medicine that is effective in the treatment of Alzheimer's disease is of great value.

SUMMARY OF THE INVENTION

As described above, in view of the deficiencies of the existing drugs, the purpose of the present invention is to provide a method for preparing medication for memory dysfunction caused by Alzheimer's disease using an extract. In particular, the extract is Puerariae Radix extract prepared by decocting Puerariae Radix in water. Puerariae Radix extract may be used in a medication for in vivo treatment of memory dysfunction in a subject, providing relief from memory disorders, anxiety and cognitive dysfunction.

Preferably, Puerariae Radix is the only Chinese herb decocted.

Preferably, the Puerariae Radix extract includes Daidzein, Daidzin and Puerarin with a ratio range of 1:1~30:50~100.

Preferably, an effective dose of Puerariae Radix extract is administered to the subject. More preferably, the effective dose is 1~1000 mg/kg.

Preferably, the frequency of administration may be four times a day to once a week; and via an injection, orally, or topically.

Preferably, effects of the Puerariae Radix extract include: reducing β-amyloid (Aβ) accumulation, hyperphosphorylation of tau protein, and neuroinflammation; and increasing the expression of synapse related proteins, the numbers of noradrenergic neurons, and the numbers of serotonergic neurons.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In the appended drawings, labels of "Puareraie radix" and "Puareriae radix extract" both represent a group treating with the extract obtained from Puareriae Radix provided in the present invention. On the other hand, regarding the immunofluorescent color photos in the appended drawings such as FIG. 1B and the others, the color of a stained region represents a staining corresponding to the word having a same color, for instance, in FIG. 1B, red regions in the photos represent a region marked by NeuN.

FIG. 1A is a timing diagram illustrating the time of cell culturing and treatment of various Chinese herbal extracts; FIG. 1B shows results of immunofluorescent staining; FIG. 1C is a bar chart illustrating relative numbers of cells expressing $NeuN^+$ protein; FIG. 1D is a bar chart illustrating relative lengths of neurites; and FIG. 1E is a bar chart illustrating relative numbers of neurites. * denotes comparison with a control group.

FIG. 2A is a timing diagram illustrating the time of cell culturing with oligomeric $A\beta_{25-35}$ and treatment of various Chinese herbal extracts; FIG. 2B shows results of immunofluorescent staining; FIG. 2C is a bar chart illustrating relative numbers of cells expressing NeuN$^+$ protein; and FIG. 2D is a bar chart illustrating relative lengths of neurites; and FIG. 2E is a bar chart illustrating relative numbers of neurites. * denotes comparison with a control group; # denotes comparison with the group treated only with $A\beta_{25-35}$.

FIG. 3A shows the western blot stain of 4HNE protein (indicates the oxidative stress level); FIG. 3B shows the quantitative results of 4HNE; FIG. 3C shows the western blot stain of deactivated GSK3β (pS9-GSK3β) protein; and FIG. 3D shows the quantitative results of the deactivated GSK3β (pS9-GSK3β) protein. * denotes comparison with the group treated with saline; # denotes comparison with the group treated only with $A\beta_{25-35}$.

FIG. 4A shows immunofluorescent staining of primary hippocampus nerve cells cultured with oligomeric $A\beta_{25-35}$ and treated with Puerariae Radix extract (500 μg/ml) and various concentrations (1%, 2% and 5%) of puerarin (the active compound of Puerariae Radix); FIG. 4B is a bar chart illustrating the relative numbers of cells expressing NeuN$^+$ protein; FIG. 4C is a bar chart illustrating the relative lengths of neurites. FIG. 4D is a bar chart illustrating the relative numbers of neurites. * denotes comparison with a control group; # denotes comparison with the group treated only with $A\beta_{25-35}$.

FIG. 6A shows spontaneous exercise ability of mice; FIG. 6B shows anxiety behavior results of mice; FIG. 6C shows the cumulative times of the mice's visit to open arms; and FIG. 6D shows analyzed results of spontaneous alternative rate. * denotes comparison with group treated with saline; # denotes comparison with the group treated only with $A\beta_{25-35}$.

FIG. 7A shows the swimming velocity of mice; FIG. 7B shows the learning curve with a training for a period of 4 days, wherein the symbols indicate: normal mice (•), mice with oligomeric $A\beta_{25-35}$ injected in the brain (○), mice with oligomeric $A\beta_{25-35}$ injected in the brain and treated with Puerariae Radix extract (Δ), and mice with saline injected in the brain and treated with Puerariae Radix extract (▼); FIG. 7C shows the analysis results of testing on day 5; and FIG. 7D shows the results of the time that the mice stay at the platform of original quadrant. * denotes comparison with group treated with saline; # denotes comparison with the group treated only with $A\beta_{25-35}$.

FIG. 8A is a western blot stain of the proteins related to tau protein phosphorylation; and FIGS. 8B to 8E show quantitative results of the proteins related to tau protein phosphorylation. * denotes comparison with the group treated with saline; # denotes comparison with the group treated only with $A\beta_{25-35}$.

FIG. 9A shows the staining results of the tau protein phosphorylation at S202 site; FIG. 9B shows the quantitative results of the hippocampus CA1 region; and FIG. 9C shows the quantitative results of the BLA region. * denotes comparison with the group treated with saline; # denotes comparison with the group treated only with $A\beta_{25-35}$.

FIG. 10A shows the staining results of 6E10; and FIG. 10B shows the quantitative results thereof. * denotes comparison with the group treated with saline; # denotes comparison with the group treated only with $A\beta_{25-35}$.

FIG. 11A shows the western blot of IDE protein; FIG. 11B shows the quantitative results thereof; FIG. 11C shows the western blot of NEP protein; FIG. 11D shows the quantitative results thereof; FIG. 11E shows the western blot of BACE1 protein; and FIG. 11F shows the quantitative results thereof. * denotes comparison with the group treated with saline; # denotes comparison with the group treated only with $A\beta_{25-35}$.

FIG. 12A shows the western blot of the NFκB and iNOS proteins; FIG. 12B shows the quantitative results of the NFκB protein; and FIG. 12C shows the results of the iNOS proteins. * denotes comparison with the group treated with saline; # denotes comparison with the group treated only with $A\beta_{25-35}$.

FIG. 13A shows the staining results of astrocyte and activated microglia in hippocampus; FIG. 13B shows the quantitative results of astrocyte; and FIG. 13C shows the quantitative results of activated microglia. * denotes comparison with the group treated with saline; # denotes comparison with the group treated only with $A\beta_{25-35}$.

FIG. 14A shows the western blot of PSD95 and synaptophysin proteins; FIG. 14B shows the quantitative results of PSD95 protein; and FIG. 14C shows the quantitative results of synaptophysin protein. * denotes comparison with the group treated with saline; # denotes comparison with the group treated only with $A\beta_{25-35}$.

FIG. 15A shows the staining results of the noradrenergic neurons and serotonergic neurons tissue slices; FIG. 15B shows the quantitative results of the serotonergic neurons in raphe nuclei; and FIG. 15C shows the quantitative results of the noradrenergic neurons in locus coeruleus. * denotes comparison with the group treated with saline; # denotes comparison with the group treated only with $A\beta_{25-35}$.

DESCRIPTION OF THE PREFERRED EMBODIMENTS

Figure 1A:
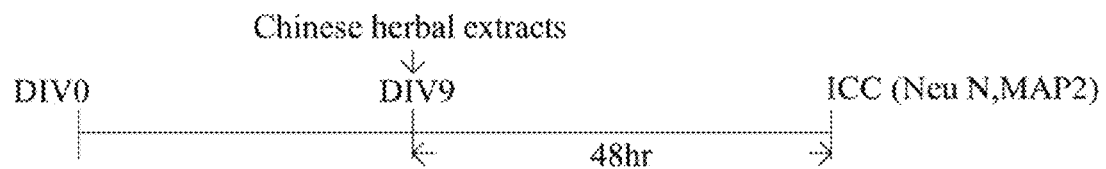
FIGS. 1A to 1E show the effects of primary hippocampus cells treated with various Chinese herbal extracts.

The present invention will be described in detail along with preferable embodiments and the drawings. It is to be noted that the experimental data disclosed in the following examples are intended to be illustrative of the technical features of the present invention and are not intended to limit the aspect in which they may be implemented.

Hereinafter, when terms such as "about" or "approximately" are used in combination with a measurable value as a variable, they indicate the assigned value of the variable, a range of values within an experimental error (for example, an average value within a 95% confidence interval), or all of the values that are within 10% of the assigned value.

Hereinafter, the terms "dosing", "administration", or "giving" mean to import a material into a subject. For instance, Puerariae Radix extract is administrated into the subject via an injection, orally, or topically, and such terms can be used alternately.

The term "subject" indicates any mammal with a need or potential need for being administered with the Puerariae Radix extract of the present invention, including: primates, rodents, pets, laboratory animals and tamed animals. For example, this may include, but is not limited to, monkeys, humans, swine, cattle, sheep, goats, horses, mice, rats, guinea pigs, hamsters, rabbits, felines, and canines. Preferably, the subject is a mouse or a human.

The term "extract" indicates to collect and refine the components from ingredients. In the present invention, preferably, the extract is obtained by decocting in water.

In an aspect of the present invention, the Chinese herbs as ingredients for extracting are provided by SUN TEN PHARMACEUTICAL Co., LTD. (Taipei, Taiwan). Such ingredients are stored after being grinded, decocted in water, concentrated and filtered with a filter. Preferably, the ingredient is Puerariae Radix.

In particular, in the extraction process, the ratio of Puerariae Radix to water may be about 1:1~1:20, preferably about 1:2~1:15, more preferably about 1:3~1:10, and yet more preferably about 1:5.

In addition, the Puerariae Radix extract may be obtained by continuously decocting Puerariae Radix in a period of about 1~300 minutes, preferably about 5~200 minutes, more preferably about 10~100 minutes, more preferably 20~50 minutes and yet more preferably about 30 minutes.

Then, the obtained Puerariae Radix extract is vaporized until the volume becomes about 0.01%~99%, preferably about 1%~75%, more preferably about 5%~50%, more preferably about 10%~30%, and yet more preferably about 20% of the original volume under room temperature, so as to obtain the concentrated Puerariae Radix extract.

Further, the Puerariae Radix extract is centrifuged at 100~10000 rpm, preferably 500~7500 rpm, more preferably 1000~5000 rpm, and yet more preferably 3000 rpm for 1~30 minutes, preferably 5~15 minutes, and yet more preferably 10 minutes. Then, the product is filtered with a 0.45 mm syringe filter.

Preferably, the product is diluted to a stock concentration of 1 g/mL, and stored at −20° C. until the product is required for use.

As mentioned above, said Puerariae Radix extract includes Daidzein, Daidzin and Puerarin as components at a ratio of about 1:1~30:50~100, preferably about 1:5~25: 60~90, more preferably about 1:10~20:70~80, and yet more preferably about 1:13.4:77.6.

Preparations of various solutions to be used for treatment or control groups in embodiments of the present invention are described as follows.

In some embodiments, oligomeric $A\beta_{25-35}$ for in vitro use is prepared by dissolving $A\beta_{25-35}$ (SigmaSI-A4559, USA) in water and left to stand at 37° C. for 4 days. Further, oligomeric $A\beta_{25-35}$ for in vivo use is prepared by dissolving said $A\beta_{25-35}$ in saline and left to stand at 37° C. for 4 days.

In some embodiments, Puerarin (purchased from Sigma-Aldrich, USA) is dissolved in a trace of DMSO, is then diluted into 12 μM, 24 μM and 60 μM by culture medium.

The culturing method of the in vitro experiments and the immunologic tissue staining analysis thereof in the embodiments of the present invention are described as follows.

In embodiments of the present invention, in vitro cell experiments are performed with mouse primary hippocampal neuron cells.

In embodiments of the present invention, mouse primary hippocampal neuron cells are cultured followed by a modification method according to prior art (Seibenhener and Wooten, 2012), including: obtaining a 16~18 day-old embryo from a C57BL/6J strain pregnant female mouse following cervical dislocation, obtaining the hippocampal tissue thereof and digesting the tissue with 0.05% trypsin at 37° C. for 15 minutes, and seeding $3 \times 10^4$ cells per well in a 48-well plate coated with Poly-L-lysine (100 μg/mL); wherein the components of the medium include: Neurobasal Medium® (Gibco; ThermoFisher Scientific, USA), and adding 2% of B-27® Additive (Gibco), 0.5 mM of glutamine (Gibco; ThermoFisher), 25 μM of glutamate (Sigma-Aldrich), 20 units/mL of Penicillin/Streptomycin Solution (Gibco™; ThermoFisher Scientific, USA), 1 mM of 4-(2-hydroxyethyl)-1-piperazineethanesulfonic acid (HEPES) (Sigma-Aldrich), and 1% of heat inactivated Donor Horse Serum (Gibco™; ThermoFisher). Primary hippocampal neuron cells are cultured in an incubator in an environment of 37° C. and 5% $CO_2$.

In some embodiments, experiments should be performed when said cells are in an Alzheimer's disease state. Hence, the inventor treats said primary hippocampal neuron cells with said oligomeric $A\beta_{25-35}$ in order to reduce the numbers of neurons and branches, and length of synapses, so that a pathological state of Alzheimer's disease may be simulated. Further, the cells were treated with various Chinese herbal medicine and Puerariae Radix extract for 1 hour and with 50 μM of oligomeric $A\beta_{25-35}$ for 48 hours. Finally, the cells are collected for performing immunofluorescent staining, and analysis of parameters such as neuron cell numbers, neurite lengths, neurite numbers, $A\beta$ amount, oxidation stress and $GSK3\beta$ amount by western blot.

The process of immunofluorescent staining analysis is described as follows: various Chinese herbal medicine are added to the mouse primary hippocampal neuron cell culture on day 9 (DIV 9) for 1 hour, and treated with $A\beta_{25-35}$ for 48 hours; the cells are fixed with 4% of paraformaldehyde (PFA) (Sigma-Aldrich) at 4° C. for 30 minutes; the cells are rinsed three times in PBST for 10 minutes so as to remove remaining PFA; the cells are blocked with 10% fetal bovine serum (FBS) and reaction is allowed to occur at 37° C. for 2 hours; NeuN (1:1000; Millipore) and MAP2 (1:1000; Millipore) primary antibodies are added and reaction is allowed to occur at 4° C. for 16 hours; then rinsing three times with PBST; reaction with secondary antibodies at room temperature for 1 hour; finally, staining nucleus with 4',6-diamino-2-phenylindole (DAPI) (Sigma-Aldrich) and analyzing neuron numbers, synapse lengths, and branch numbers with a High Content Micro-Imaging Acquisition and Screening System and MetaXpress (purchased from Molecular Devices).

In particular, the subject, routes of administration, evaluation methods of the behavior of the subject and the pathological analysis methods used in embodiments of the present invention are described in details as follows.

In embodiments of the present invention, the subjects may be mice.

As mentioned above, the mice may be C57BL/6J strain, 8-week-old pregnant female mice and 12-week-old male mice (purchased from National Laboratory Animal Center, Taiwan). The breeding environment is configured as 20-25° C., 60% relative humidity and 12 hours circadian rhythm. All experiments were performed from 7 am to 7 pm, and comply with the provision pursuant to the regulations stipulated by the Committee of Care and Use of Laboratory Animals of National Taiwan Normal University.

In embodiments of the present invention, the frequency of administration of the Puerariae Radix extract into a subject may be once per week, preferably once every six days, preferably once every five days, preferably once every four days, preferably once every three days, preferably once every two days, preferably four times a day, preferably three times a day, preferably twice a day and more preferably once a day.

Further, in some embodiments of the present invention, C57BL/6J strain male mice (12 weeks old) are used as a subject. After mice have been allowed to adapt to their environment over 6 days, mice are anesthetized with Avertin (0.4 g/kg; purchased from Sigma-Aldrich). The mice are fixed on a stereotactic apparatus for operation, followed by an injection of oligomeric $A\beta_{25-35}$ (10 nM, 3 μL) into both sides of hippocampus CA1 (AP: −0.23 mm relative to bregma; ML: ±0.2 mm relative to midline; DV: −0.15 mm relative to skull). Puerariae Radix extract and same volume of vehicle (saline) are intraperitoneal (i.p.) injected once per day from day 6, the day before said operation, for 31 days (day 6 to day 36). On day 24, the OF (open field) test is performed; on day 26, EPM (elevated plus test) is performed; on day 28, Y-maze is performed; on days 30 to 36, MWM (Morris water maze) is performed; and on day 37, mice are sacrificed for pathological analysis.

Accordingly, the dose of the administrated Puerariae Radix extract is about 1~1000 mg/kg, preferably about 10~800 mg/kg, preferably 100~500 mg/kg, more preferably 200~400 mg/kg, and yet more preferably about 340 mg/kg.

Accordingly, the volume of the administrated Puerariae Radix extract is about 1~750 4, preferably 10~500 4, more preferably 50~250 4, and yet more preferably 100 μL.

In an embodiment, OF Test is performed to said mice. The mice are placed in a central area of a white box (30 cm×30 cm×30 cm). Then, mice are allowed to walk spontaneous for 10 minutes, and the time that mice stay at the central area (15 cm×15 cm×15 cm) in first 5 minutes are recorded. Since mice tend to stay at periphery area of an open field when anxious, observing the staying time in the central zone of the mice can determine the anxiety level of the mice. In addition, the total distance that the mice moved in last 5 minutes may be used to determine an index of spontaneous exercise ability of the mice. After finishing the test of each mouse, the box was wiped with 70% and 30% (v/v) of ethanol to remove remaining odor in order to avoid affecting other test results.

In an embodiment, EPM (elevated plus maze) is performed to said mice. By observing the characteristic of exploring in unfamiliar environment and the contradictory and conflicting behavior caused by fear of highly hanging arms of an animal, the anxiety level of the animal can be determined. The EPM is arranged by two relative open arms (30 cm×5 cm) and two relative enclosed arms (30 cm×5 cm×15 cm) connected with a central area (10 cm×10 cm), wherein the material thereof is matte acrylic. Each mouse is placed at the central area facing the open arms and is allowed to spontaneously and freely explore for 5 minutes. After finishing the test of each mouse, the box was wiped with 70% and 30% (v/v) of ethanol to remove remaining odor in order to avoid affecting other test results. The total staying time at the open arms of each mouse is recorded by a video tracking system (Noldus).

In an embodiment, Y Maze is performed to said mice. Taking advantages of the characteristic that mice tend to explore unfamiliar environment, short-term spatial memory of mice can be measured by means of a Y maze module arrangement of three arms (35 cm×5 cm×20 cm) formed in white acrylic. The mice are placed in the middle of three arms of the Y Maze, thereby the mice are allowed to spontaneously and freely explore for 8 minutes, wherein one count is recorded when four limbs of the mice completely entered any one of three arms, The formula is described as follows: The spontaneous alternative rate=count of single instances of entering into any one of three arms×100/(total entering counts−2).

In an embodiment, MWM is performed to said mice. MWM is a test for observing spatial learning and memory of the mice by searching a platform in a wide pool. Since mice do not like staying in water, and it is also hard for mice to swim, mice will instinctively find a place to rest (the platform) while in the water. The behavior of finding the platform relates to a complex memory process within the brain, including 1) collecting the visual information (such as shape information of rectangle, circle and triangle) with respect to spatial positioning, and 2) processing, sorting, memorizing, fixing and recalling said information. In particular, mice are placed in a pool filled with milky white pigment without toxicity (it is used to make water become opaque and hide the platform so that mice are unable to know the position of the platform at the beginning), and are allowed to explore the platform (fixed in a predetermined quadrant) underwater. The test distinguishes several phases as follows: 1) exploring phase: Place the mouse in the water for 1 minute. If the mouse cannot find the platform in time, then grab the mouse and make it stand on the platform for 20 seconds. Finally, place the mouse at a dry place and allow to rest until next experiment; 2) Acceptance phase: place the mouse into the water maze at four specific positions in turn in order to test whether the mouse can find the platform or not. Such training is repeated four times a day and continued for 4 days (each mouse is trained 16 times in total). After 4 days of training, the learning ability of the mice in testing is measured. After 24 hours of the last testing trial, the platform is removed and allow the mice to spontaneously and freely swim in the pool so as to observe whether the mice remembers the position of the platform or not (long-term spatial memory test). The swimming path is recorded with a CCD camera and analyzed with an image tracking system (EthoVision-XT).

In an embodiment, immunohistochemical staining analysis is performed to said mice. The inventor collects the brain tissue by perfusion followed by fixing and dehydrating. Then, obtains 30 pm frozen sections by a freezing microtome (CMS3050S, Leica). The section is rinsed with PBS for 10 minutes and is repeated three times so as to remove mounting gel; then, endogenous peroxidase is removed by H$_2$O$_2$. Next, destroy non-specific antigen with a blocking solution for 1 hour, then add in primary antibody (6E10, pS202Tau, ChAT, 5-HT, TH, GFAP, Ibal) and allow to react for 12 hours. Next, add in secondary antibody (dilute 200 times in the blocking solution, Vector Laboratories, USA) and allow to react for 1 hour. After that, detect avidin-biotin complex (ABC) after 1 hour stained. Finally, colorate by a DAB-kit (DAB: diaminobenzidine; Vector Laboratories, USA). After all sections are stained, they are fixed on a slide, dried, dehydrated, mounted, and photographed for quantity (performed by Image Pro Plus, Meida Cyberetics, USA).

In the aforementioned embodiment, the results of two groups are compared with an independent sample t-test. Results of three or more groups are compared with a one-way ANOVA test, and post hoc tests are analyzed by LSD (SPSS version 20; Illinois, USA). All of the results are indicated by Mean±SEM. Further, statistically significance is achieved when p<0.05.

On the other hand, particularly, in the embodiments of the present invention, Puerariae Radix extract may include functions of reducing the β-amyloid (Aβ) accumulation, hyperphosphorylation of tau protein, and neuroinflammation, and increasing the expression of synapse related proteins, the numbers of noradrenergic neurons and the numbers of serotonergic neurons.

The embodiments of the present invention disclosed above have been implemented and the results are stated below. According to the results, the purposes, features and advantages of the present invention are easily realized. A person skilled in the art will understand that the results do not limit the scope of the present invention. Further, the reasonable error of the results should be presented when repeating.

Figure 1B:
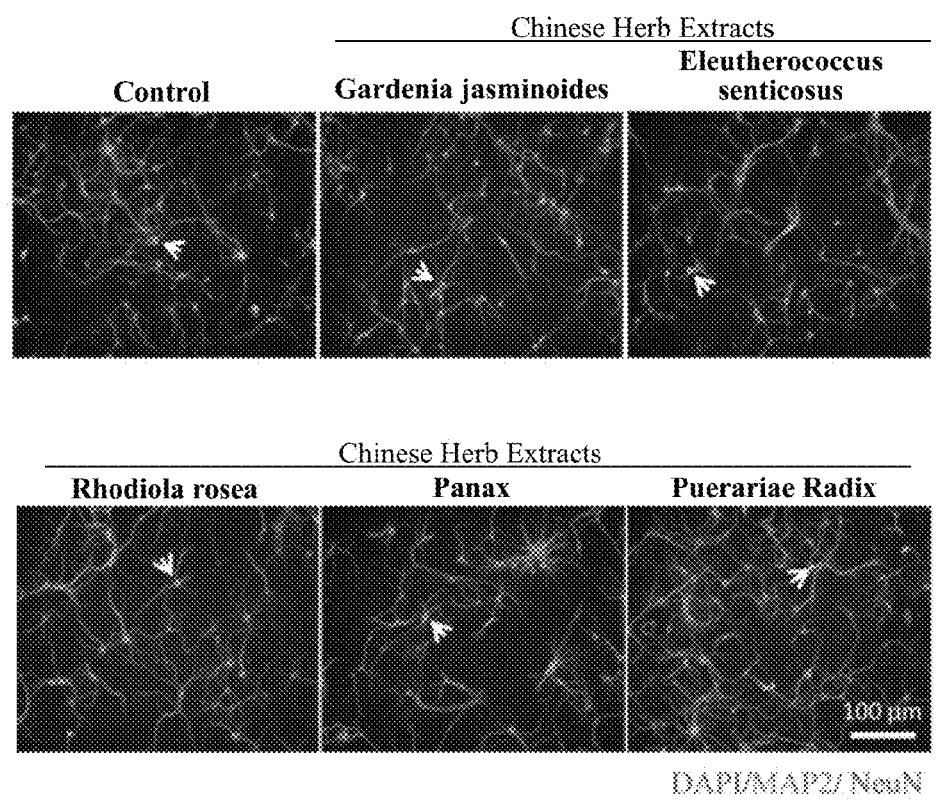
Figure 1C:
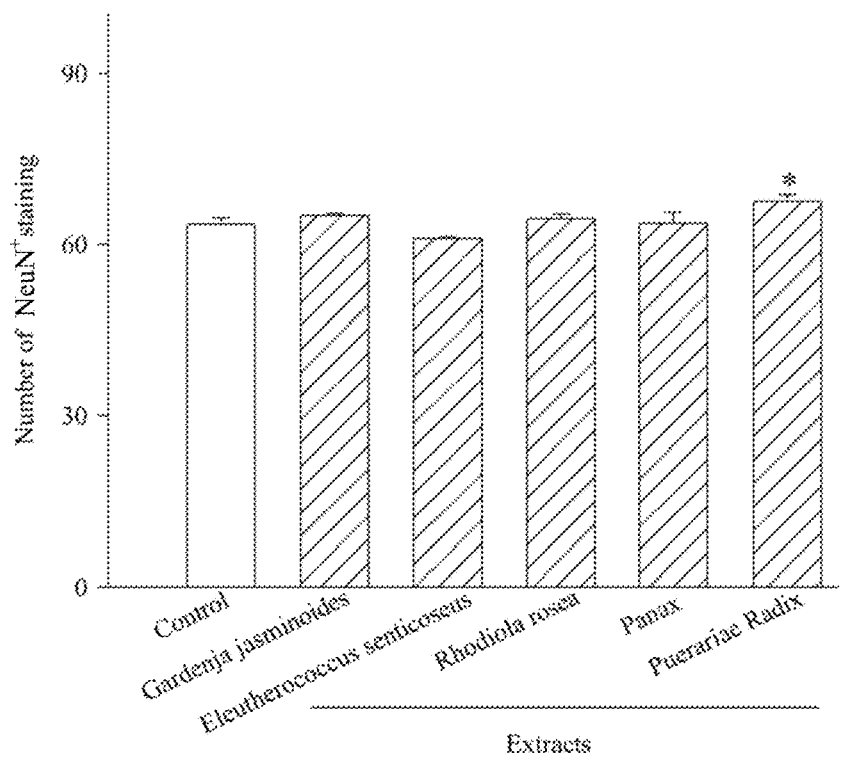
Figure 1D:
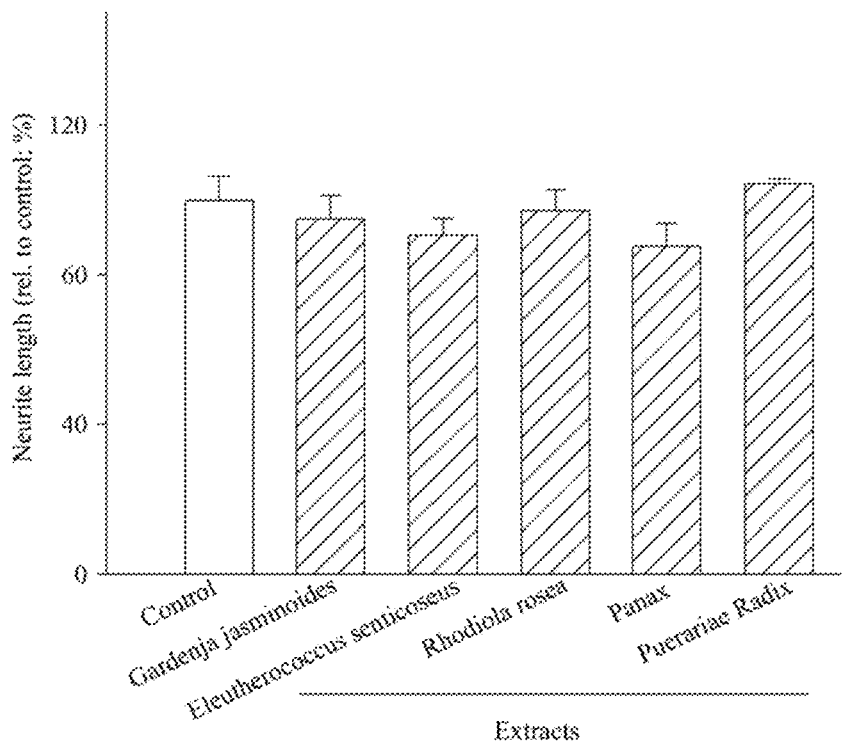
Figure 1E:
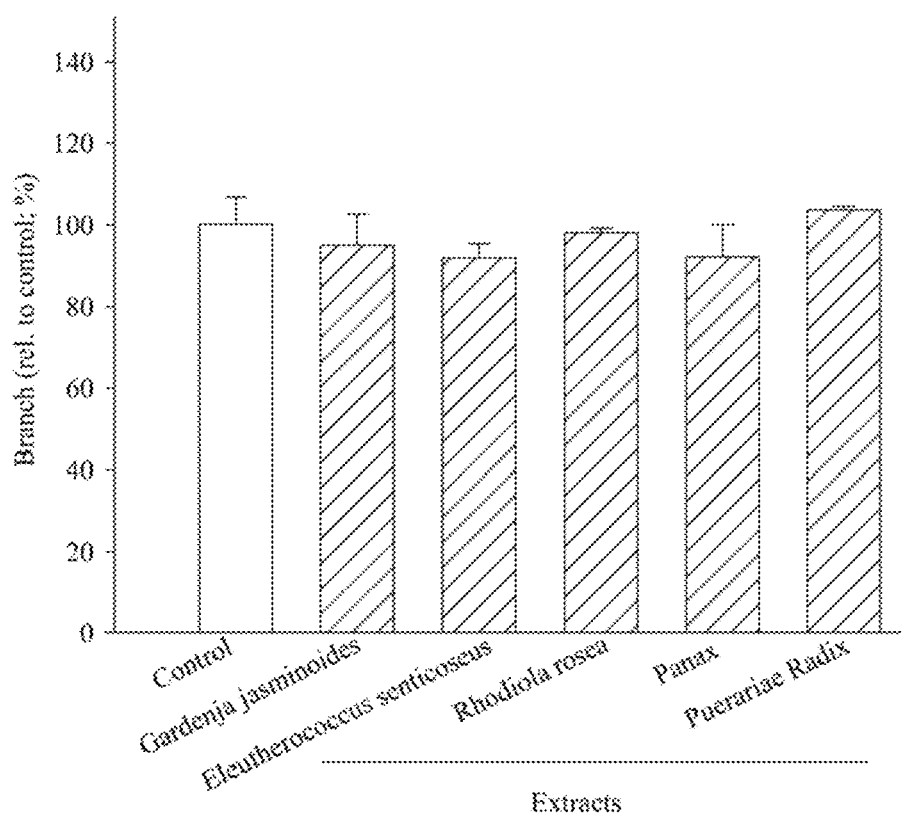
Figure 2A:
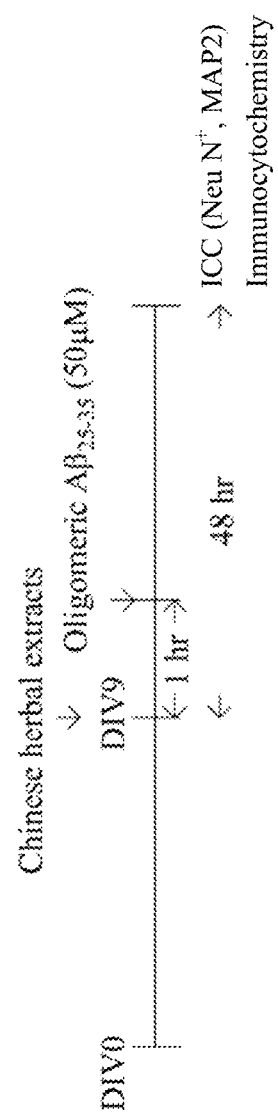
FIGS. 2A to 2E show the effects of treatment with several Chinese herbal extracts on primary hippocampus nerve cells cultured with oligomeric $A\beta_{25-35}$.
Figure 2B:
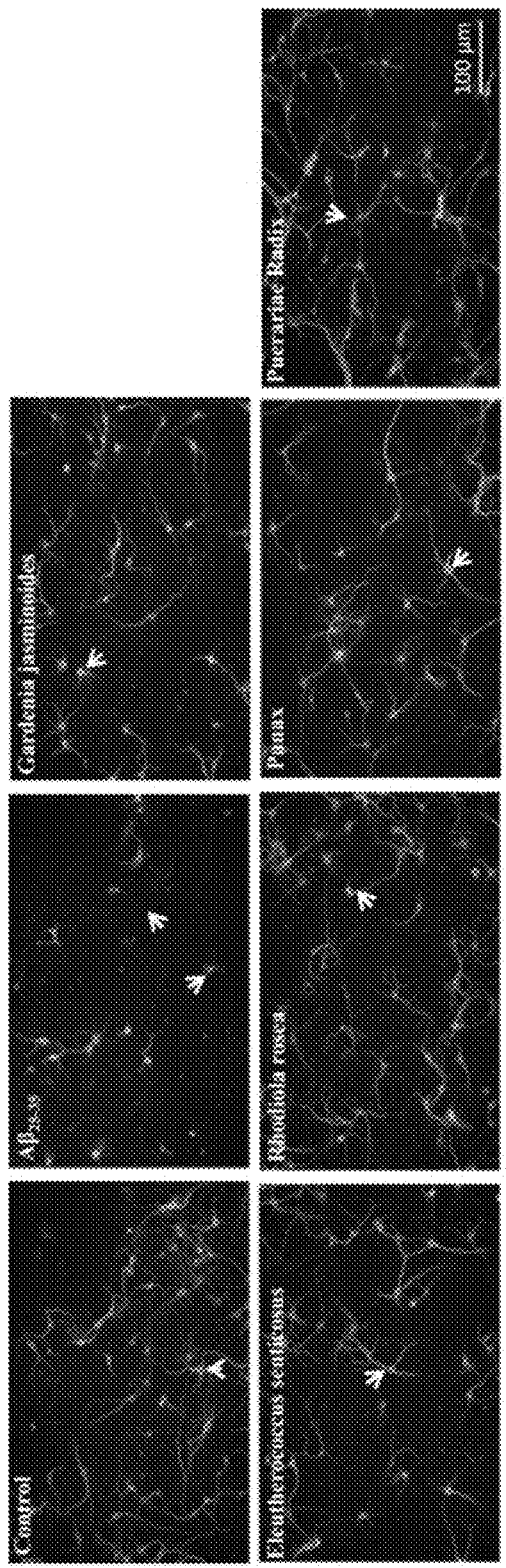
Figure 2C:
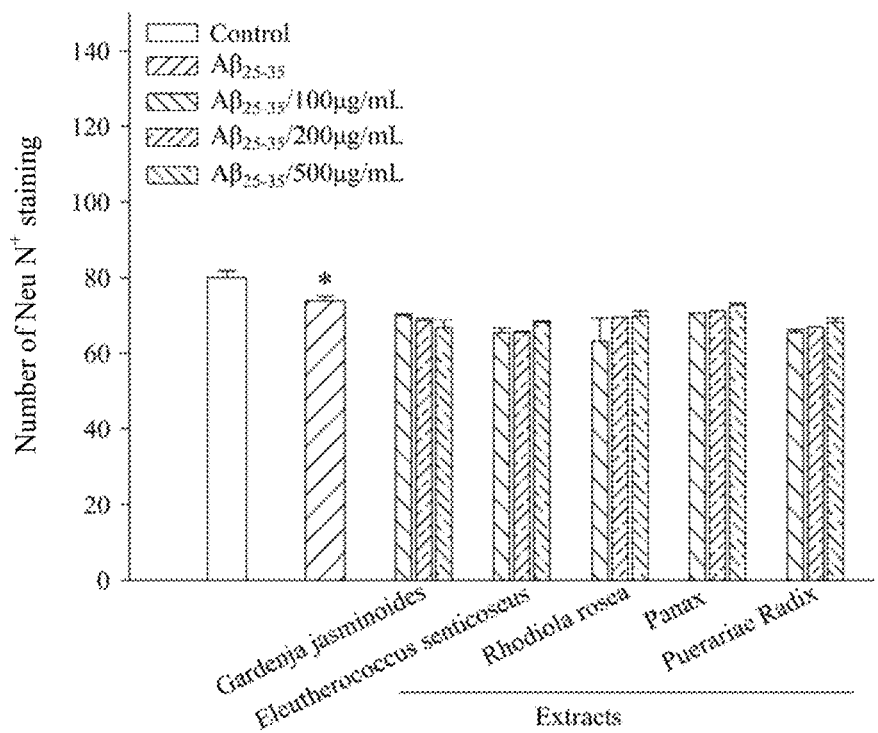
Figure 2D:
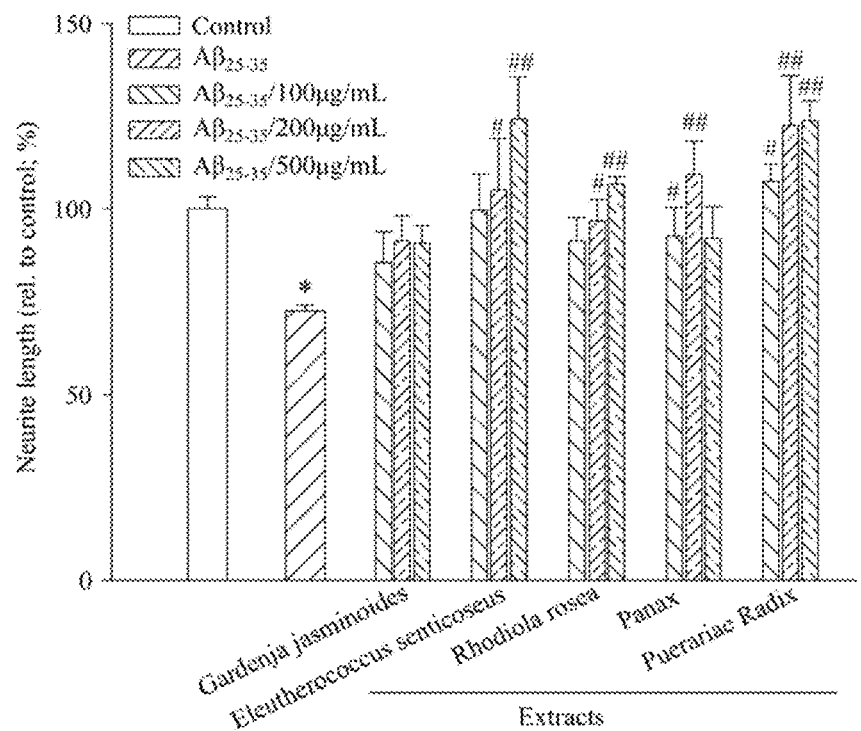
Figure 2E:
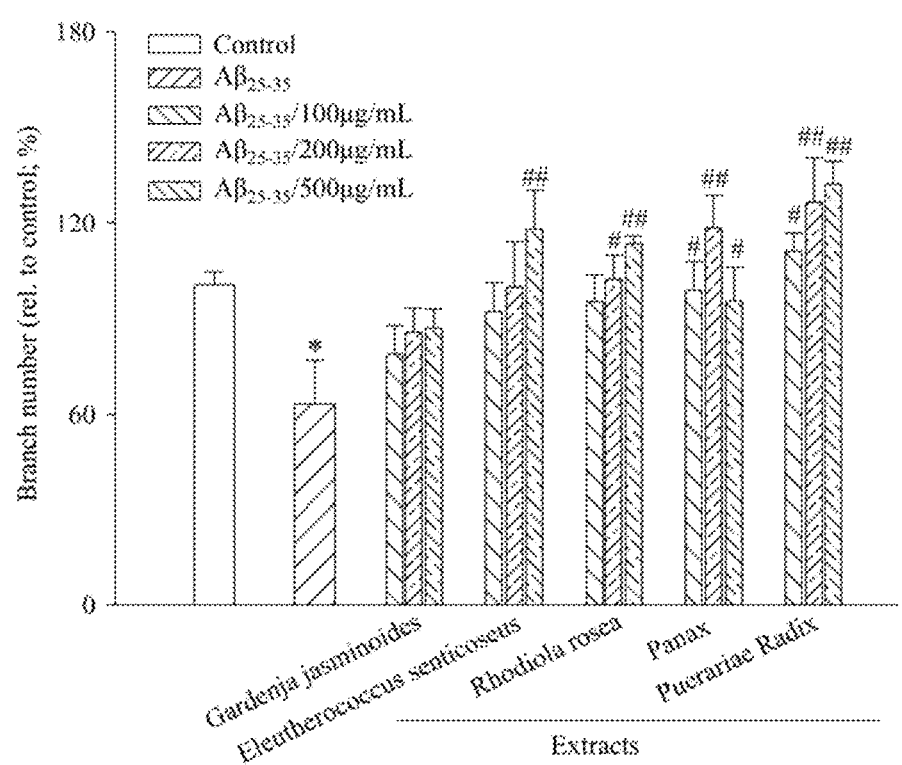

According to FIGS. 1A to 1E, administrating various Chinese herbal medicines to the primary hippocampal cell culture does not affect the numbers of neurons (FIGS. 1B and 1C), length of neurites (FIGS. 1B and 1D) and numbers of branches (FIGS. 1B and 1E). The above results show that the used Chinese herbal medicines do not damage neurons.

On the other hand, FIGS. 2A to 2E show that numbers of neurons (FIGS. 2B and 2C), lengths of neurites (FIGS. 2B and 2D) and numbers of branches (FIGS. 2B and 2E) of the group treated with oligomeric Aβ$_{25-35}$ are significantly lower than that of the control group which is not treated with oligomeric Aβ$_{25-35}$. The result proves that oligomeric Aβ$_{25-35}$ definitely damages the primary hippocampal neuron cells. Further, the inventor found that pre-treating with no matter what kind of Chinese herbal medicine does not increase the number of neurons (FIGS. 2B and 2C) when compared to the group treated only with oligomeric Aβ$_{25-35}$. With regards to neuron cell morphology, the group treated with no matter what concentration of Puerariae Radix extract has a significantly increase in the lengths of neurites (FIGS. 2B and 2D) and numbers of branches (FIGS. 2B and 2E) when compared with the group treated only with oligomeric Aβ$_{25-35}$. However, such neuron protecting effect induced by other kinds of Chinese herbal medicines is lower than that induced by the Puerariae Radix extract. Hence, in terms of administrating in an oligomeric Aβ$_{25-35}$ pre-treated platform, the Puerariae Radix extract does provide a level of neuron protecting effect.

Figure 3A:
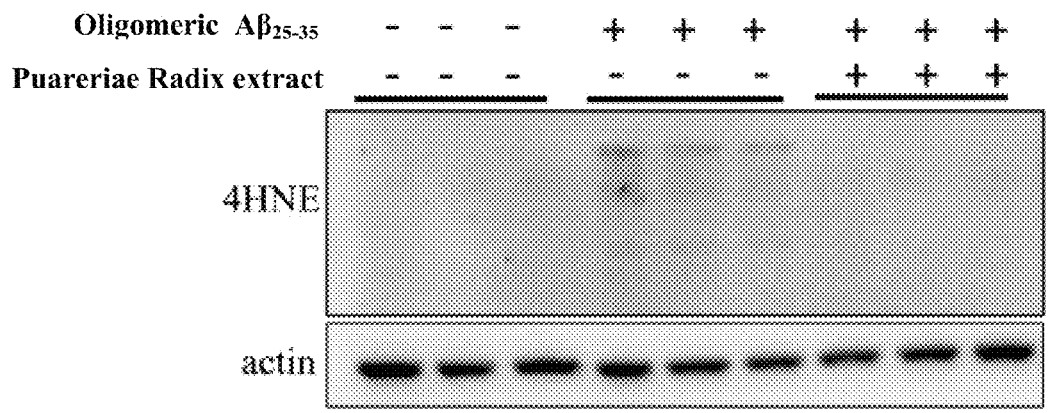
FIGS. 3A to 3D show western blot results which analyze the oxidation stress and deactivated GSK3β expression in a primary hippocampus nerve cell culture pre-treated with Puerariae Radix extract.
Figure 3B:
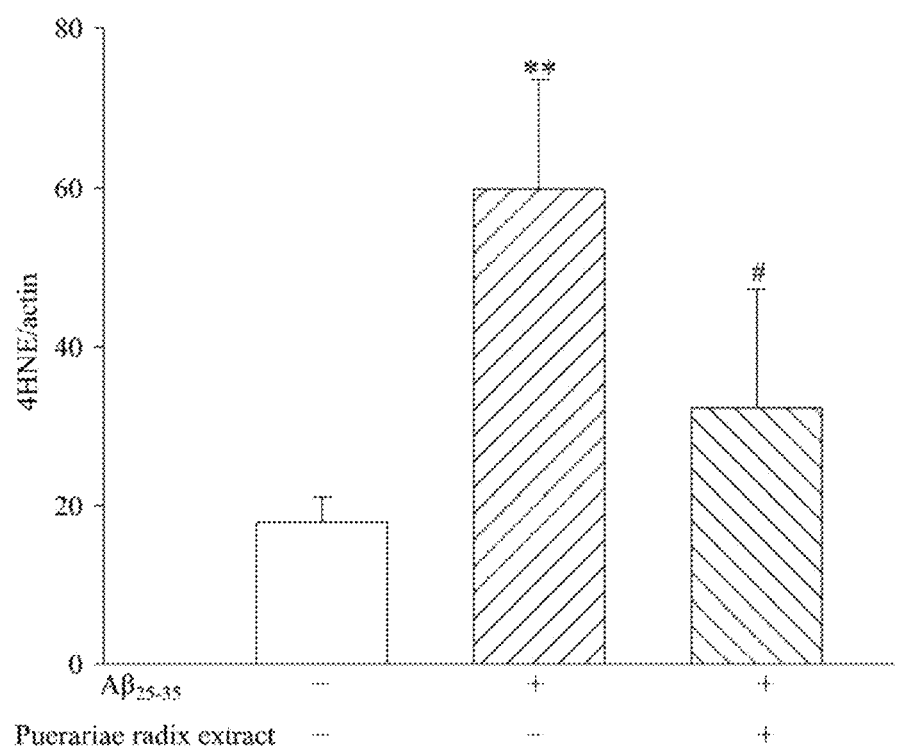
Figure 3C:
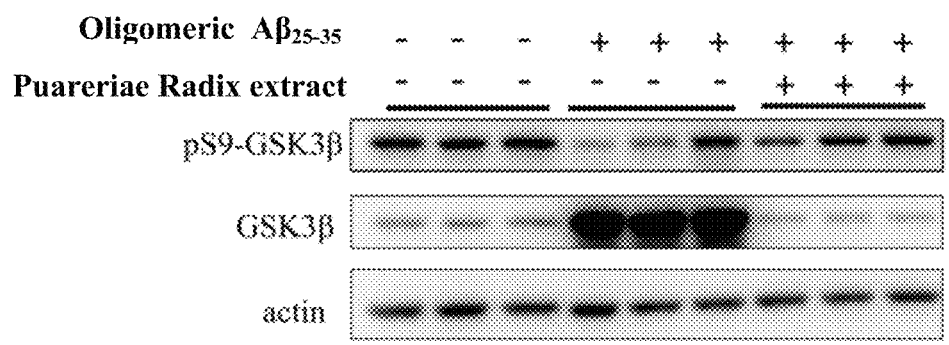
Figure 3D:
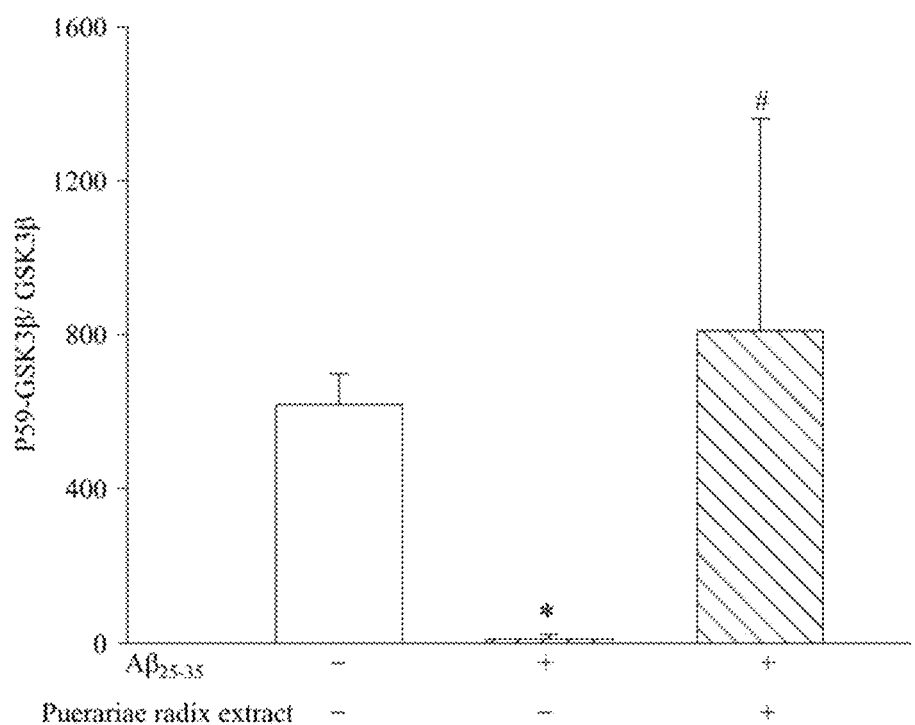

Furthermore, the inventor analyzed the molecular mechanism of the neuron protecting effect induced by the Puerariae Radix extract within the oligomeric Aβ$_{25-35}$ pre-treated platform. The results are illustrated in FIG. 3, which show that the treatment of oligomeric Aβ$_{25-35}$ significantly increases the expression of 4HNE, a marker for oxidative stress (lipid peroxidation) (FIGS. 3A and 3B), whereas the treatment of the Puerariae Radix extract significantly reduces the expression of 4HNE (FIGS. 3A and 3B). GSK3β is an important kinase known to be involved in the phosphorylation of tau protein. The inventor analyzed the expression of the phosphorylated GSK3β, for instance, pS9-GSK3β (deactivated GSK3β). According to the quantitative results, it was found that the expression of pS9-GSK3β is significantly lower than that of the control group (FIGS. 3C and 3D) after the treatment of oligomeric Aβ$_{25-35}$. However, after the administration of the Puerariae Radix extract, the expression is significantly increased (FIGS. 3C and 3D). Thus, this indicates that the Puerariae Radix extract is able to improve anti-oxidation stress and the expression of deactivated GSK3β.

Figure 4A:
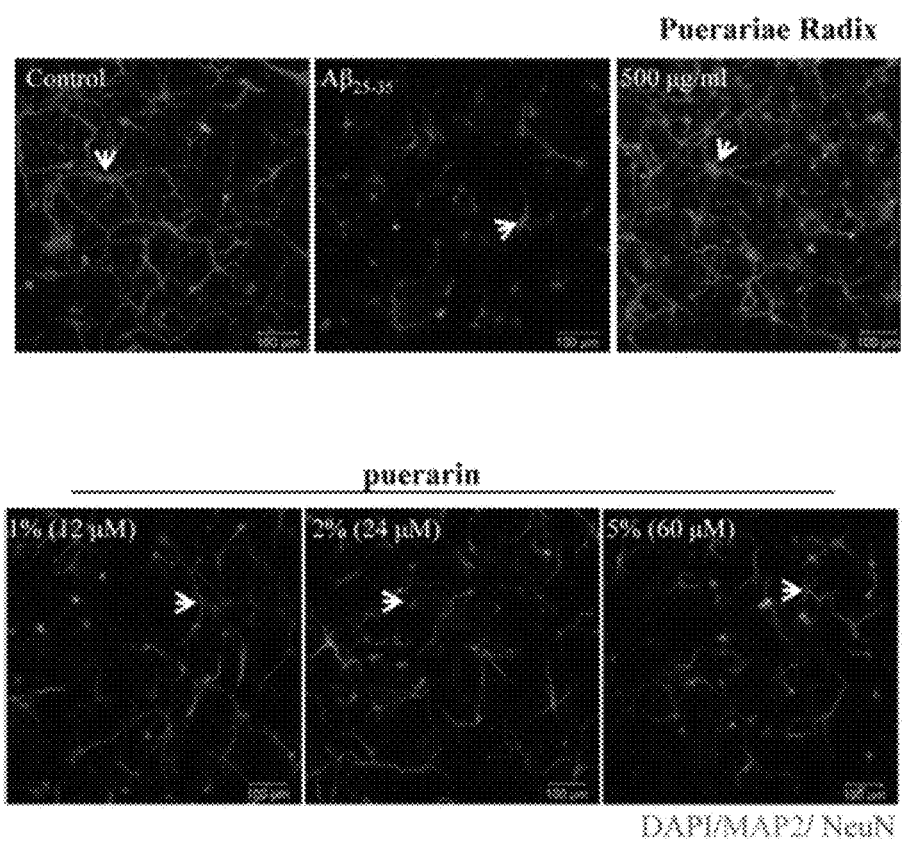
FIGS. 4A to 4D show the effects of treatment with various concentrations of Puerariae Radix extract on primary hippocampus nerve cells cultured with oligomeric $A\beta_{25-35}$.
Figure 4B:
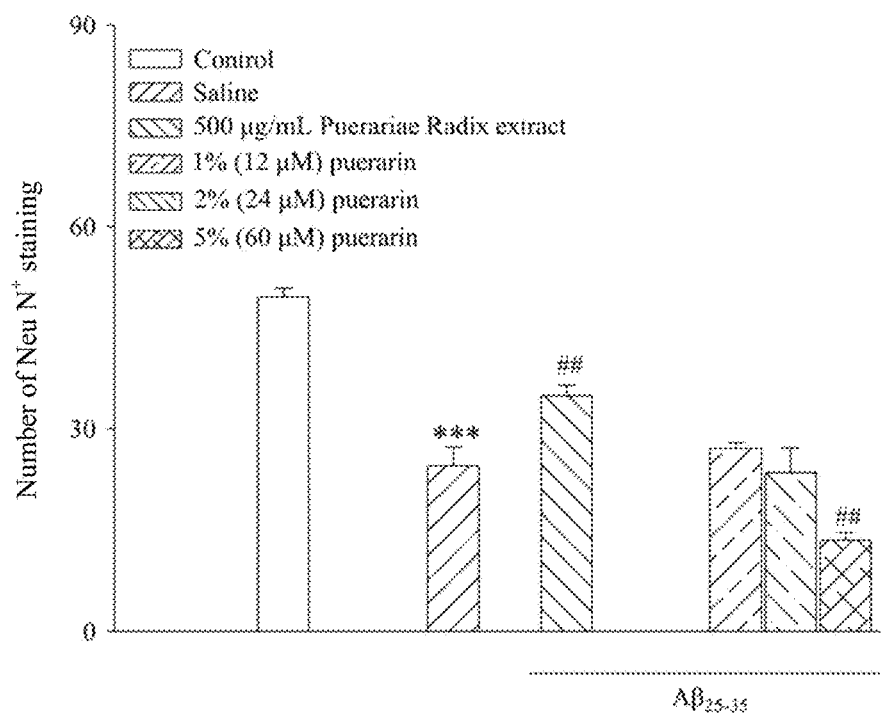
Figure 4C:
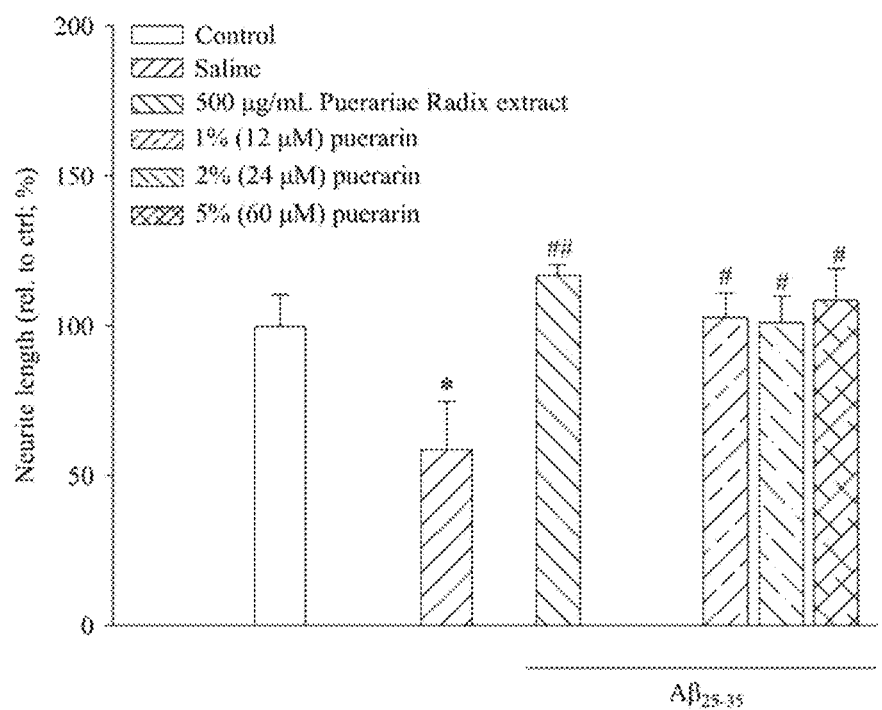
Figure 4D:
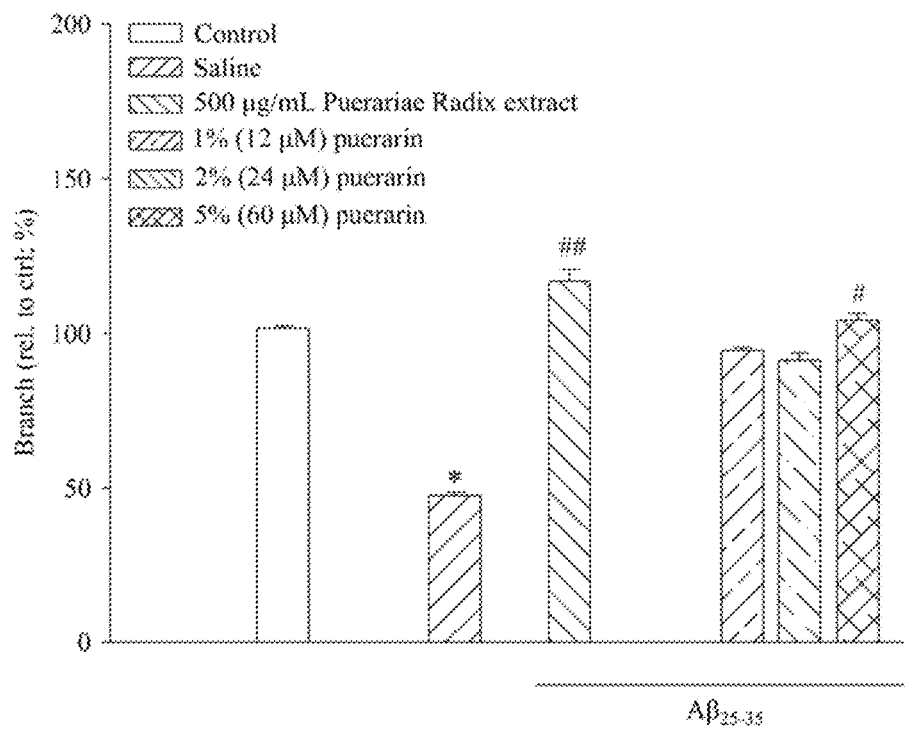

In addition, for further realizing whether the neuron protecting effect of the Puerariae Radix extract is higher that Puerarin or not, the inventor compared the Puerariae Radix extract with various concentrations of Puerarin, wherein the Puerariae Radix extract includes 2% of Puerarin, and the Puerarin contained in 500 μg/mL of the Puerariae Radix extract is about 24 μM and are known according to the pre-analyzed HPLC results. Regarding FIGS. 4A to 4E, numbers of neurons (FIGS. 4B and 4C), lengths of neurites (FIGS. 4B and 4D) and numbers of branches (FIGS. 4B and 4E) of the Puerariae Radix extract treated groups are higher than the groups treated with 12 μM, 24 μM, and 60 μM of Puerarin. It shows that the Puerariae Radix extract of the present invention provides higher therapeutic effect that Puerarin alone under a same amount of Puerarin.

Figure 5:
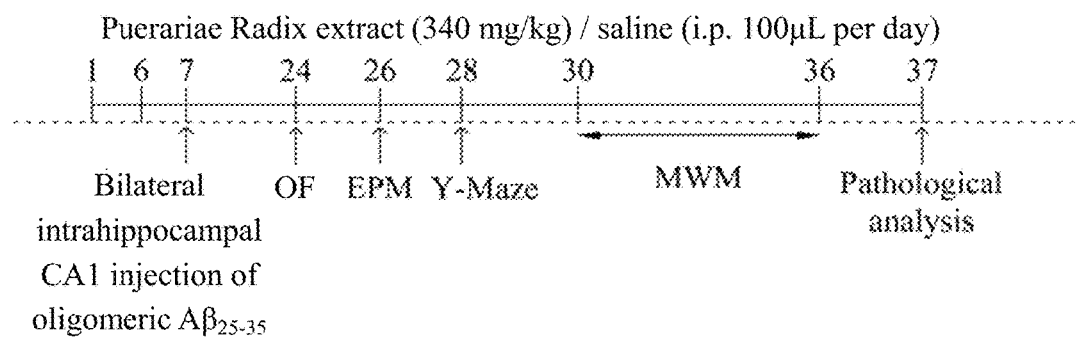
FIG. 5 illustrates the process of in vivo experiments. The Puerariae Radix extract (340 mg/kg; 100 μL/day) is administrated to a subject by intraperitoneal injection (i.p.). The control group was injected with same volume (100 μL) of saline.

FIG. 5 is a timing diagram of in vivo studies. After the mice purchased from the animal center have been allowed to adapt to the experimental environment for 6 days, the inventor injects oligomeric Aβ$_{25-35}$ (10 nM, 3 μL) into both sides of hippocampus CA1 (AP: −0.23 mm relative to bregma; ML: ±0.2 mm relative to midline; DV: −0.15 mm relative to skull) on day 7. Puerariae Radix extract or same volume of vehicle (saline) are intraperitoneal (i.p.) injected once per day from day 6, the day before said operation, for 31 days (day 6 to day 36). On day 24, the OF test is performed; on day 26, EPM is performed; on day 28, Y maze is performed; on days 30 to 36, MWM is performed; and on day 37, mice are euthanized for pathological analysis.

Figure 6A:
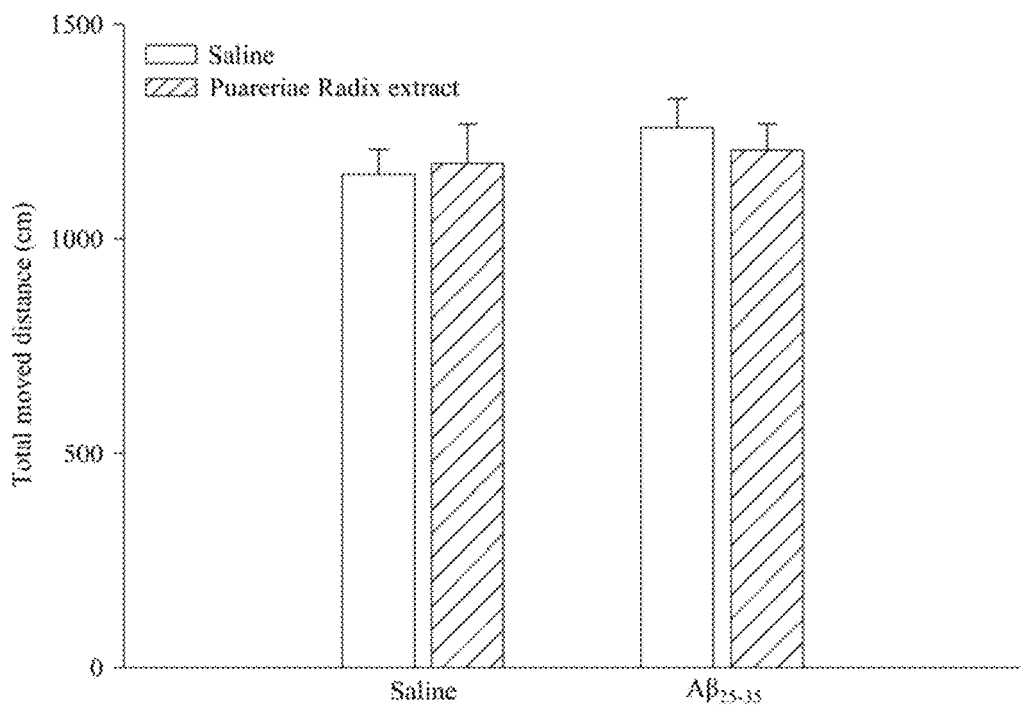
FIGS. 6A to 6D illustrate the results of the Open Field (OF) test, Elevated Plus Maze (EPM) test and Y maze test.
Figure 6B:
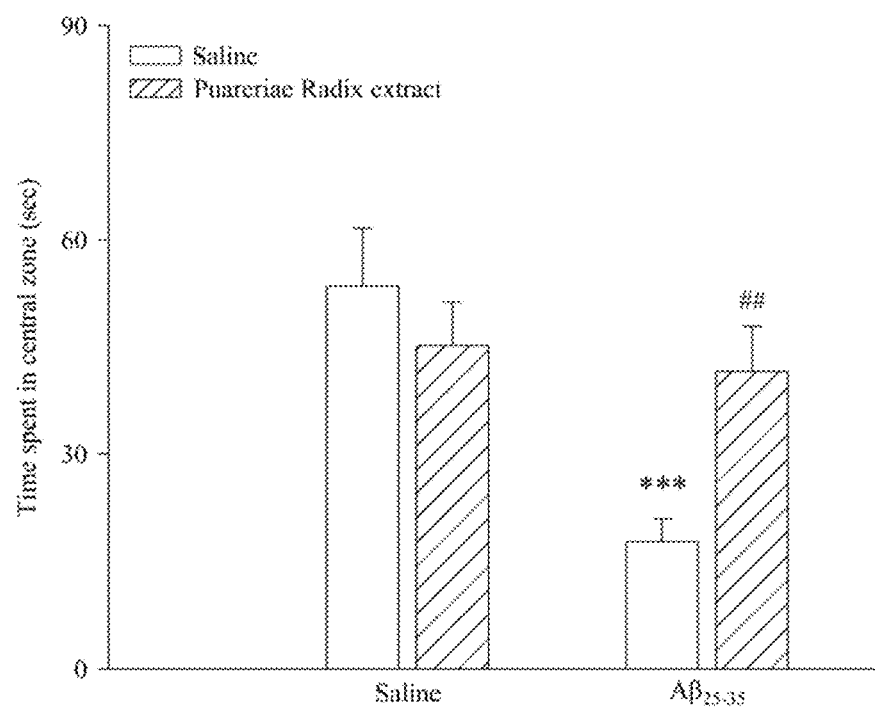
Figure 6C:
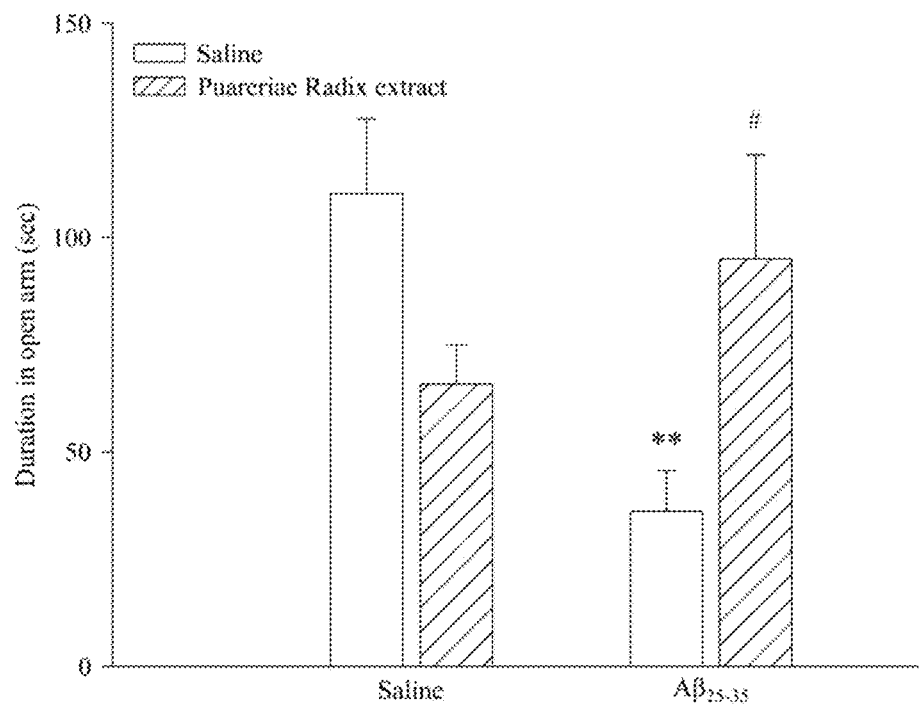

On the other hand, no matter injecting oligomeric Aβ$_{25-35}$ or saline to hippocampus CA1, and whether administrating the Puerariae Radix extract or not, they do not affect the spontaneous exercise ability of mice (FIG. 6A). In addition, the inventor has also found that the mice injected with oligomeric Aβ$_{25-35}$ within the hippocam pus CA1 stays a longer time at the central area (10 cm×10 cm) than the mice injected with saline (FIG. 6B). Whereas the time stayed at the central area is significantly increases for mice administrated with the Puerariae Radix extract (FIG. 6B). That is, the administration of Puerariae Radix extract is able to relieve the anxiety behaviors caused by oligomeric Aβ$_{25-35}$. Similarly, according to the results of EPM test, the inventor has found that the mice injected with oligomeric Aβ$_{25-35}$ within the hippocampus CA1 stay a shorter time at the open arms than the mice injected with saline, whereas the time stayed at the open arms is significantly decreased for mice administrated with the Puerariae Radix extract (FIG. 6C). According to such results, the Puerariae Radix extract can relieve the anxiety behaviors caused by oligomeric Aβ$_{25-35}$.

Figure 6D:
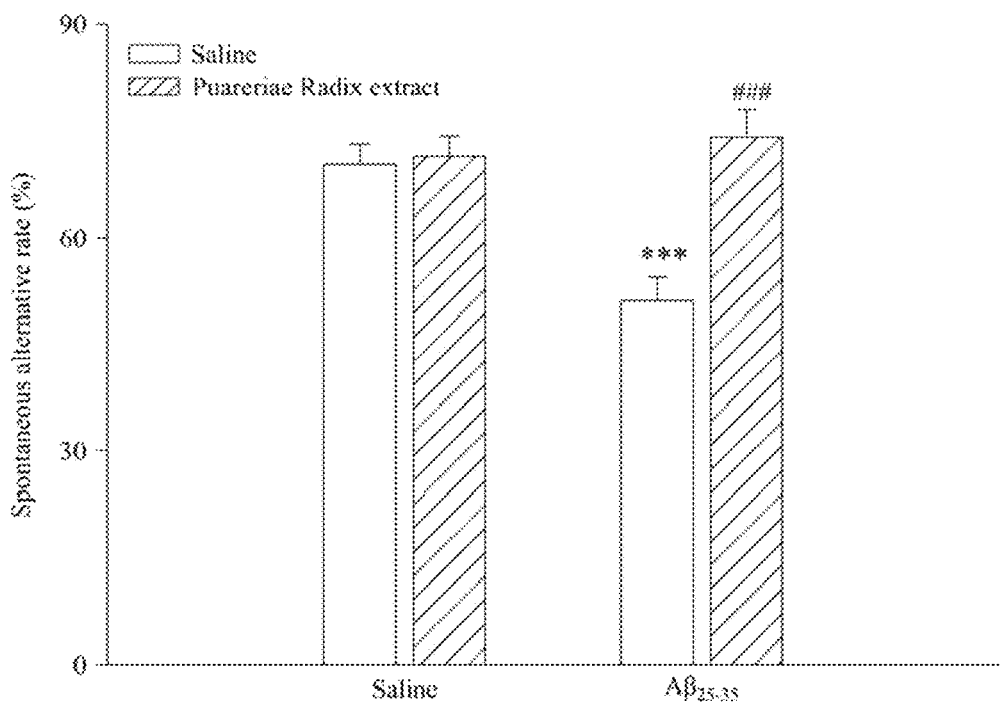

Additionally, the Y Maze test results show that injecting oligomeric Aβ$_{25-35}$ may cause significant damage to short-term memory (FIG. 6D). However, the spontaneous alternative rate of the group administrated with the Puerariae Radix extract is significantly higher than that of the group treated only with oligomeric $A\beta_{25-35}$. This shows that the Puerariae Radix extract is able to provide relief from damage to short-term memory caused by oligomeric $A\beta_{25-35}$.

Figure 7A:
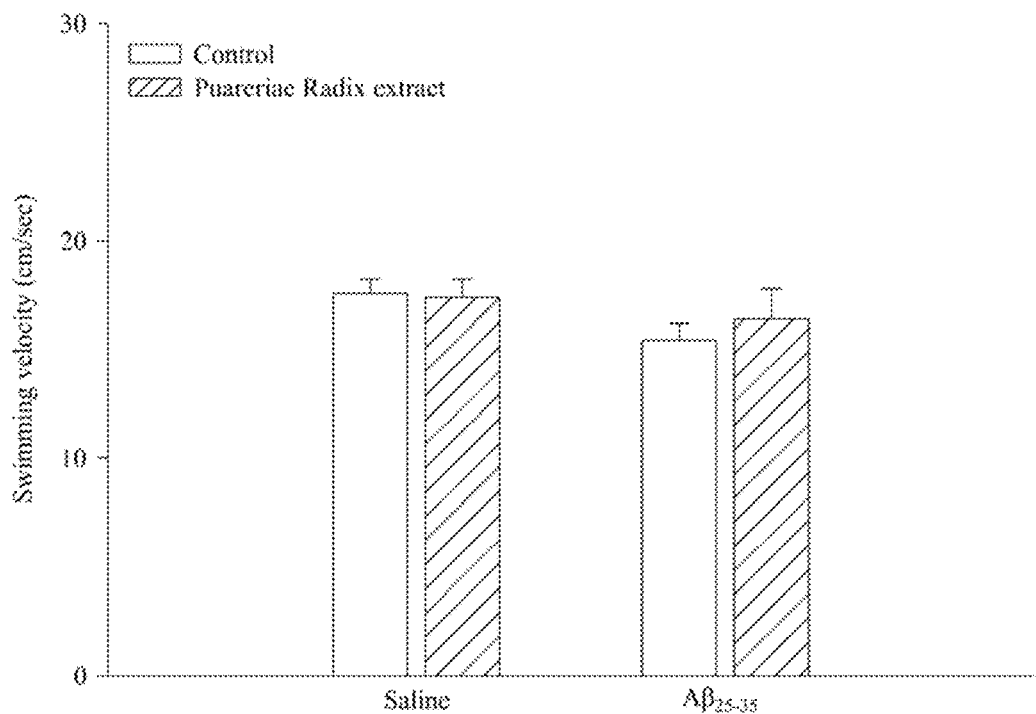
FIGS. 7A to 7D show the results of the Morris water maze (MWM) task.
Figure 7B:
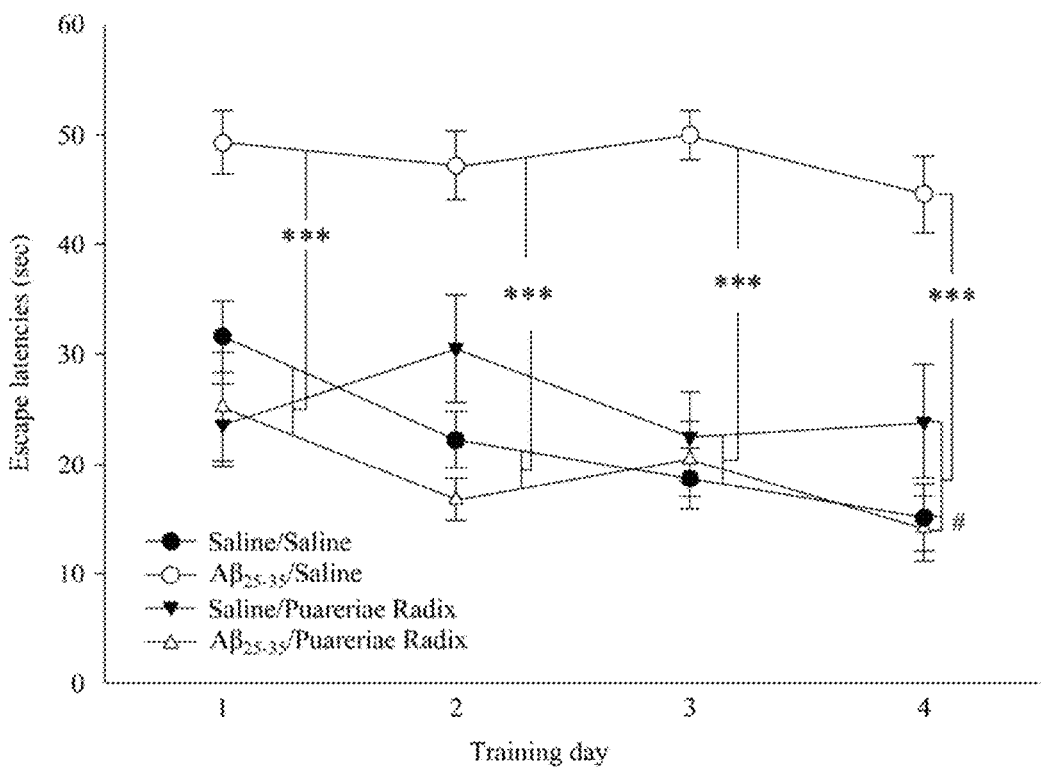
Figure 7C:
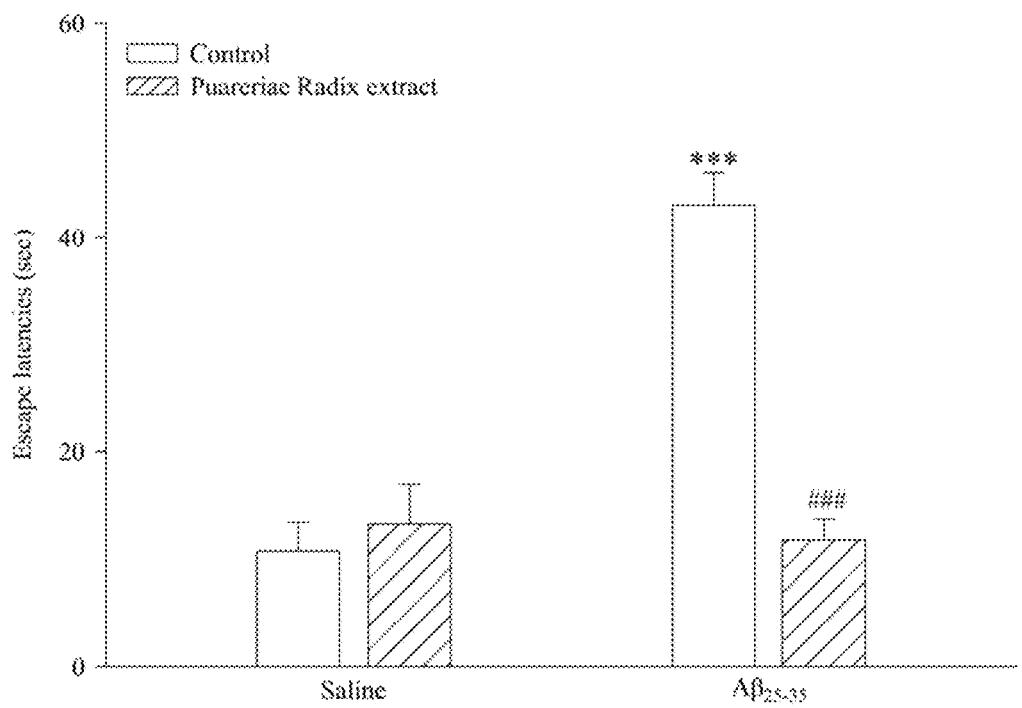
Figure 7D:
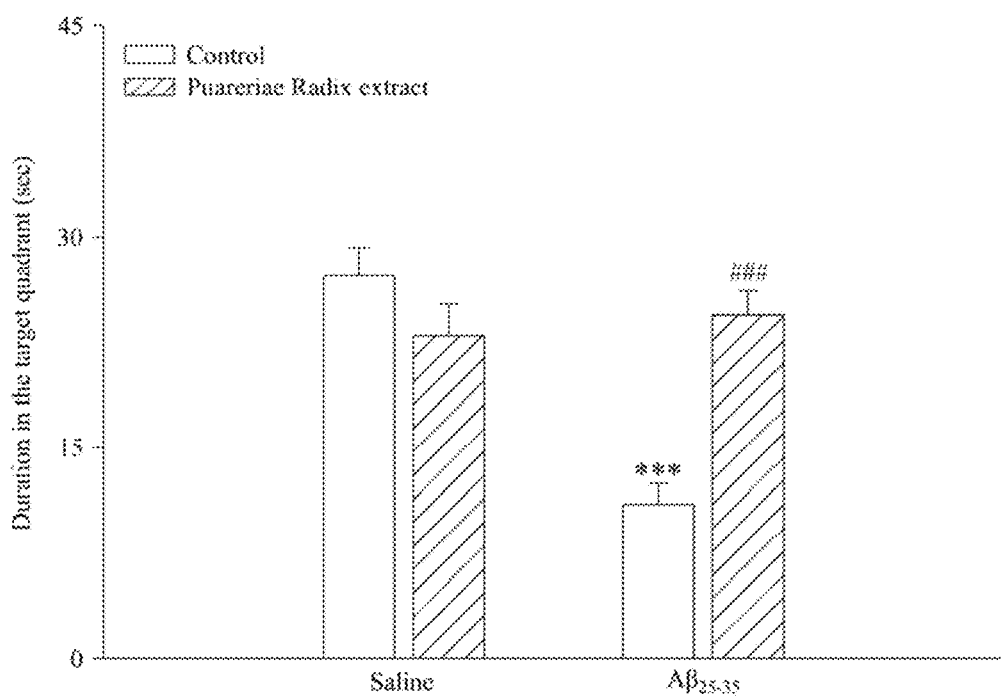

According to the results of the MWM test, the swimming velocity of the mice is shown in FIG. 7A, which illustrates that mice of different groups swim at a same velocity in the water maze, that is, their innate body strengths are approximately the same. FIG. 7B shows the learning curve of the mice performing in a training trial in a period of 4 days. Accordingly, injecting saline into the brain of normal mice does not affect their learning ability so that the results show an effective curve (•); the time that the mice injected with $A\beta_{25-35}$ into the hippocampus CA1 thereof (○) required for arriving to the platform is not reduced depending on increasing number of training dates (FIG. 7B); Furthermore, although the administration of the Puerariae Radix extract does not reduce the time required for arriving to the platform (▼) (FIG. 7B), the time that the mice is administered with the Puerariae Radix extract required for arriving to the platform on day 4 is significant reduced in comparison with that on day 1 (FIG. 7B). In addition, it terms of the mice injected with oligomeric $A\beta_{25-35}$ into the hippocampus CA1 thereof, wherein the time that the mice administrated with the Puerariae Radix extract (Δ) required for arriving to the platform is significantly lower than that of the mice administrated with saline (FIG. 7B). After four days of training, the testing was performed on day 5, and the time required for arriving to the platform is recorded. The spatial learning ability of the mice was determined according to the results. The inventor has found the time that the group injected with oligomeric $A\beta_{25-35}$ into the hippocampus CA1 thereof required for arriving to the platform is significantly increased in comparison with that of the group injected with saline (FIG. 7C); whereas the group administrated with the Puerariae Radix extract required for arriving to the platform is significantly decreased in comparison that of the group administrated with saline (FIG. 7C). After 24 hours from the last trial of the testing, the platform is removed and the time that the mice stayed at the quadrant used to place the platform (target quadrant) is calculated for evaluating the long-term memory. According to the results, the time stayed at the target quadrant of the group is injected with oligomeric $A\beta_{25-35}$ into the hippocampus CA1 is significantly decreased in comparison with that of the group injected with saline (FIG. 7D); the time in which the group administrated with the Puerariae Radix extract stayed at the target quadrant is significantly increased in comparison with that of the group administrated with saline (FIG. 7D). Therefore, the MWN test results shows that injecting oligomeric $A\beta_{25-35}$ into the hippocampus CA1 of mice causes damage to memory and spatial learning, whereas the administrating the Puerariae Radix extract is able to relieve the level of such damage.

Figure 8A:
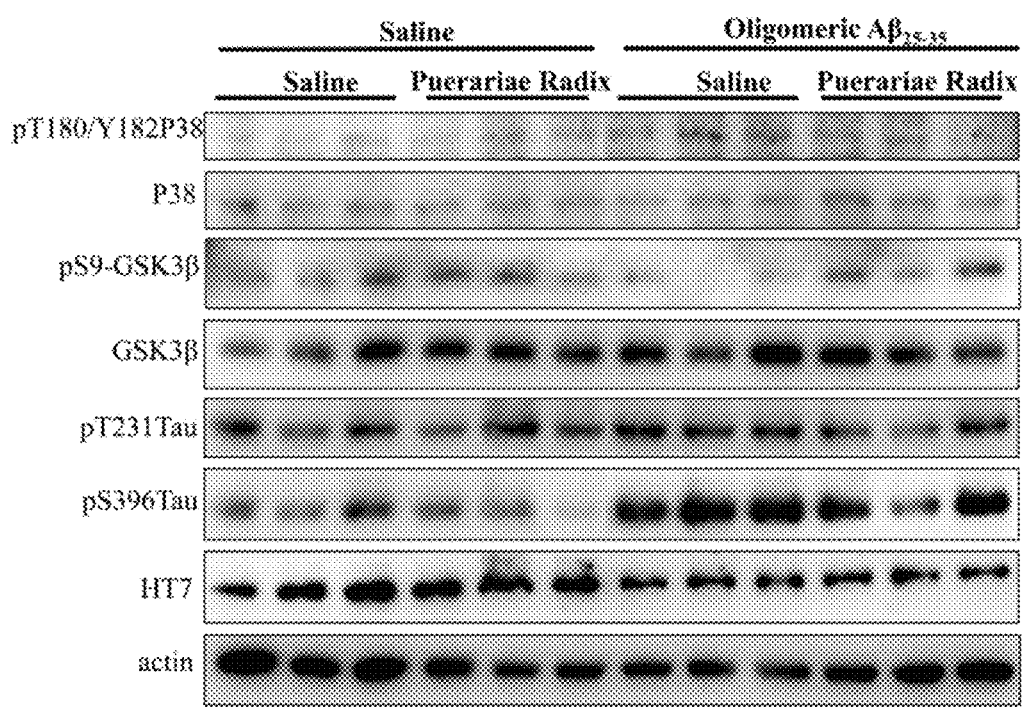
FIGS. 8A to 8E show the analysis results of proteins related to tau protein phosphorylation.
Figure 8B:
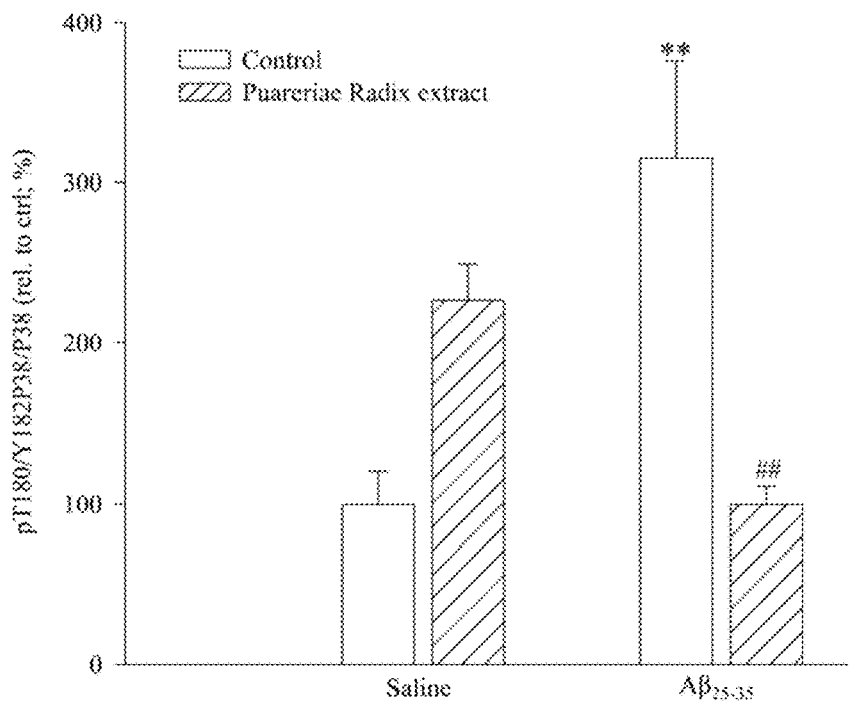
Figure 8C:
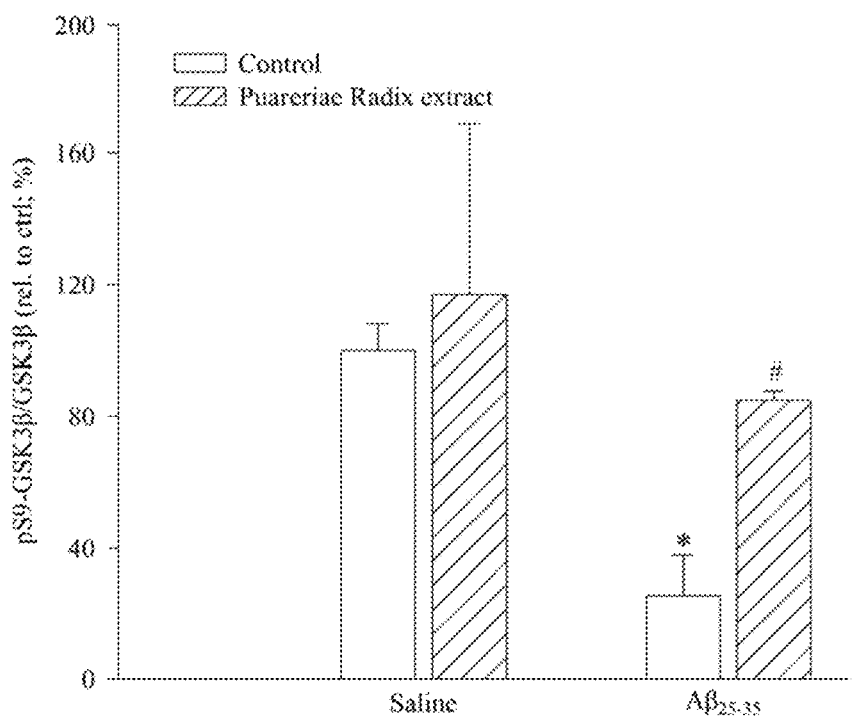
Figure 8D:
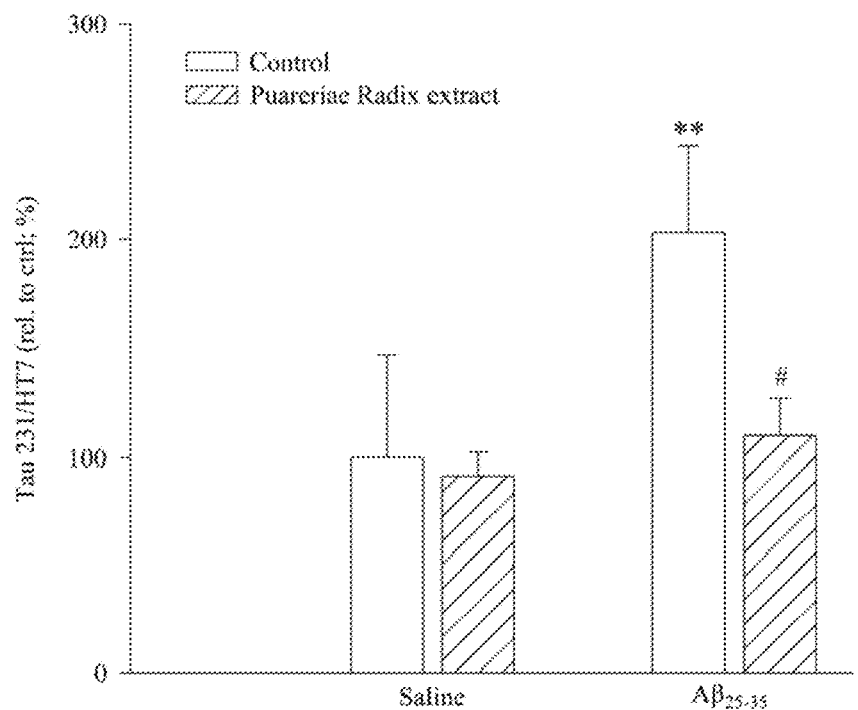
Figure 8E:
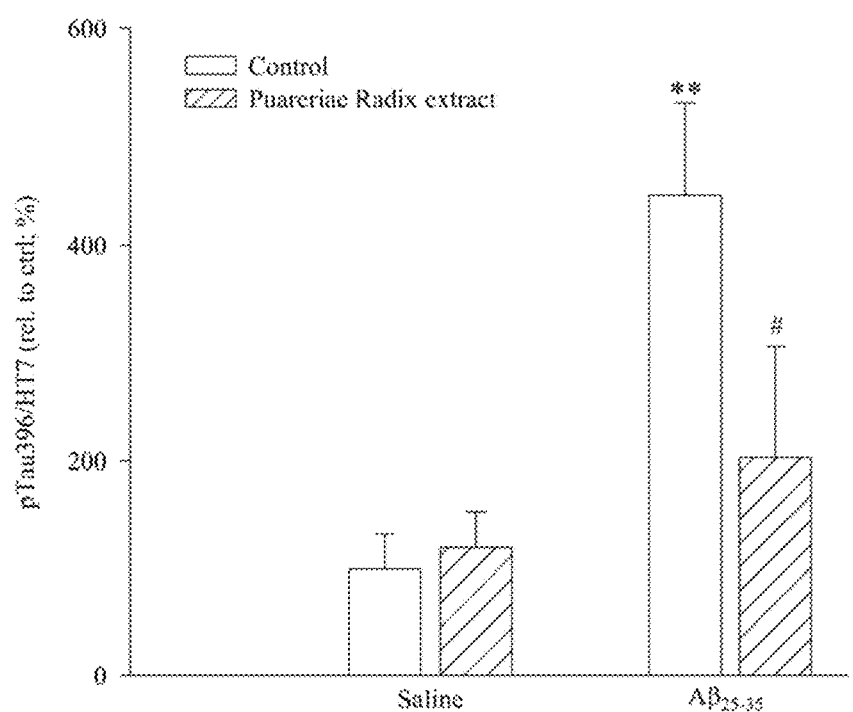
Figure 9A:
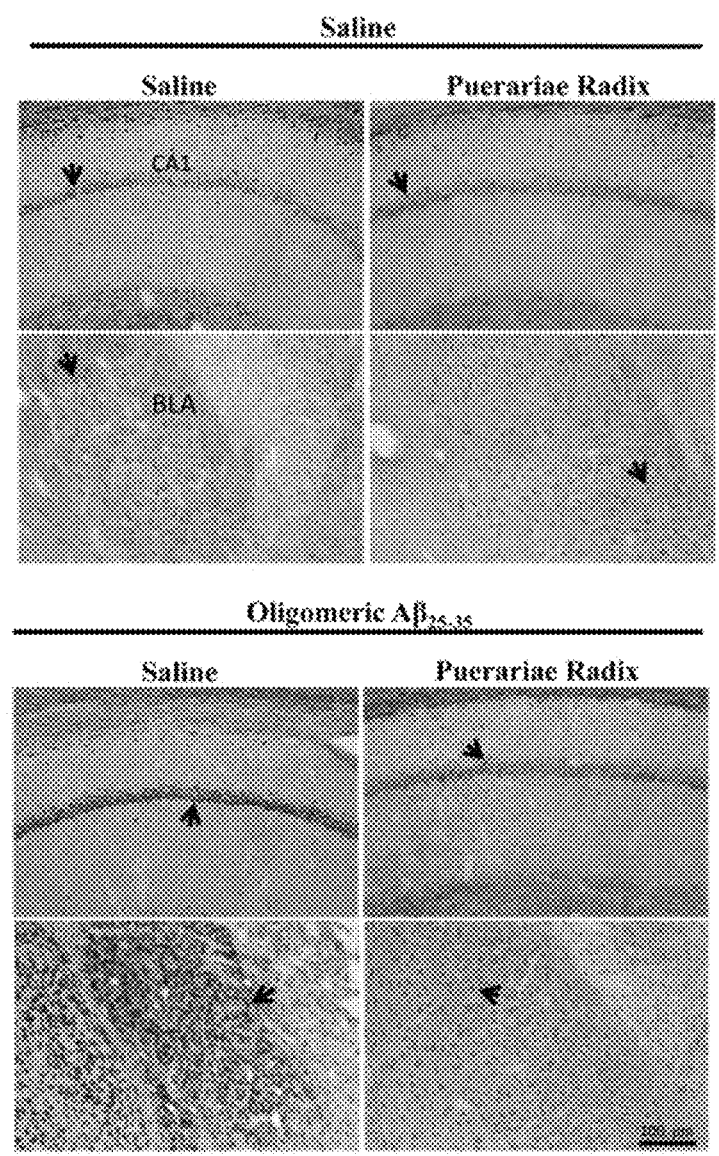
FIG. 9A to 9C show immunohistochemical staining results of the tau protein phosphorylation at Ser202 (S202) site in hippocampus CA1 and basolateral nucleus amygdala (BLA) region.
Figure 9B:
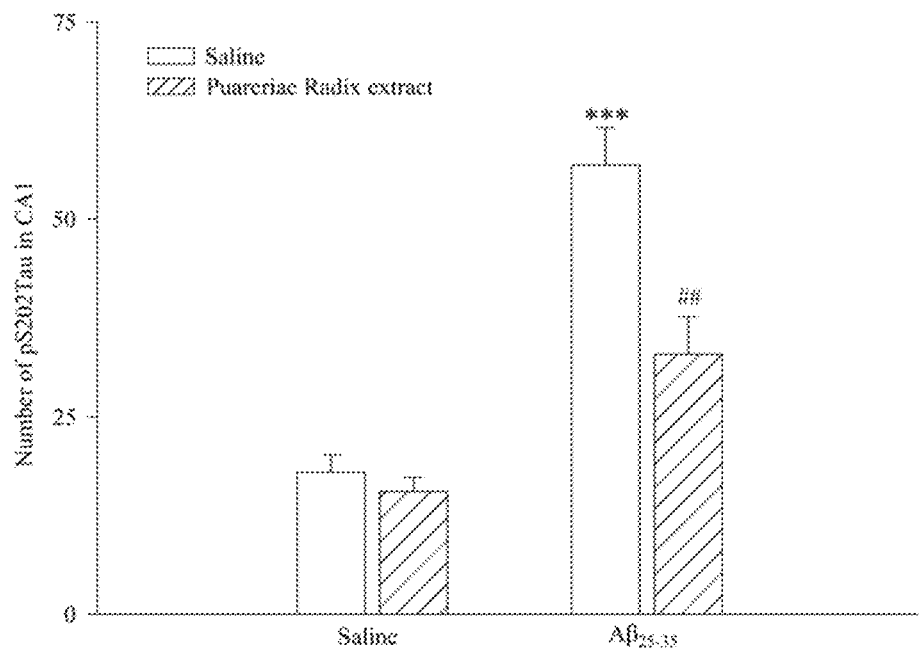
Figure 9C:
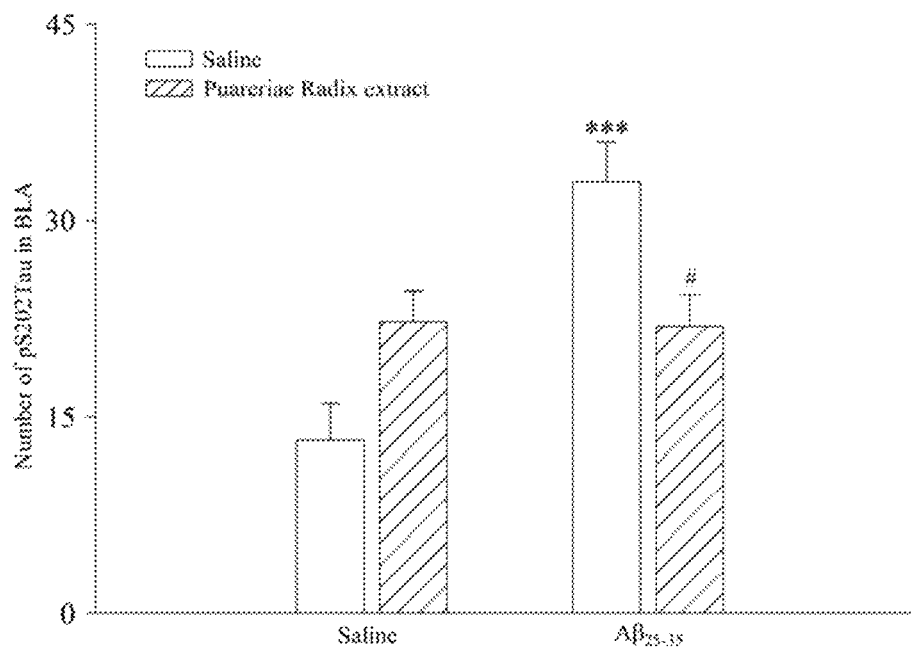

Similarly, the Puerariae Radix extract is able to relieve the activation of hyperphosphorylation of tau protein in neuron cells caused by oligomeric $A\beta_{25-35}$. In particular, the expression of phosphorylated P38 (pT180/Y182P38) in the group treated with oligomeric $A\beta_{25-35}$ is significantly higher than that of the group treated with saline; whereas the expression of pT180/Y182P38 in the group pretreated with the Puerariae Radix extract is significantly decreased (FIGS. 8A and 8B). Such results show that oligomeric $A\beta_{25-35}$ causes the increasing of pT180/Y182P38, whereas the Puerariae Radix extract is able to provide relief from this situation. Further, the inventor has analyzed the expression of pS9-GSK3β (inactive form of GSK3β). The results show that the oligomeric $A\beta_{25-35}$ causes a significant decrease in the expression of pS9-GSK3; whereas the expression of pS9-GSK3 is significantly increased after pretreatment with the Puerariae Radix extract (FIGS. 8A and 8B). Furthermore, the inventor has also analyzed the expression of the phosphorylation of tau protein at various sites. It was found that oligomeric $A\beta_{25-35}$ significantly increases the expression of the phosphorylation of tau protein at Thr231 and Ser396 sites (FIGS. 8A and 8B); whereas the expression of the phosphorylation of tau protein at Thr231 and Ser396 sites (FIGS. 8A and 8B) decreases after pretreatment with the Puerariae Radix extract (FIGS. 8A and 8B). Further, an immunohistochemical staining of the hippocampus of the mice was prepared to analyze the phosphorylation condition of tau protein at Ser 202 site (pS202Tau, FIG. 9). The results show that the expression pS202Tau of the group injected with oligomeric $A\beta_{25-35}$ into CA1 is significantly increased; whereas the pretreatment of the Puerariae Radix extract is able to effectively reduce the hyperphosphorylation of tau protein at Ser202 site FIGS. 9A to 9B. In addition, regarding the expression of tau protein in basolateral nucleus amygdala (BLA), the inventor has found that oligomeric $A\beta_{25-35}$ causes the phosphorylation of tau protein at Ser202 site in BLA (FIGS. 9A and 9C); whereas the expression of pS202Tau in the group pretreated with the Puerariae Radix extract is significantly lower than that in the group treated with saline (FIGS. 9A and 9C).

Figure 10A:
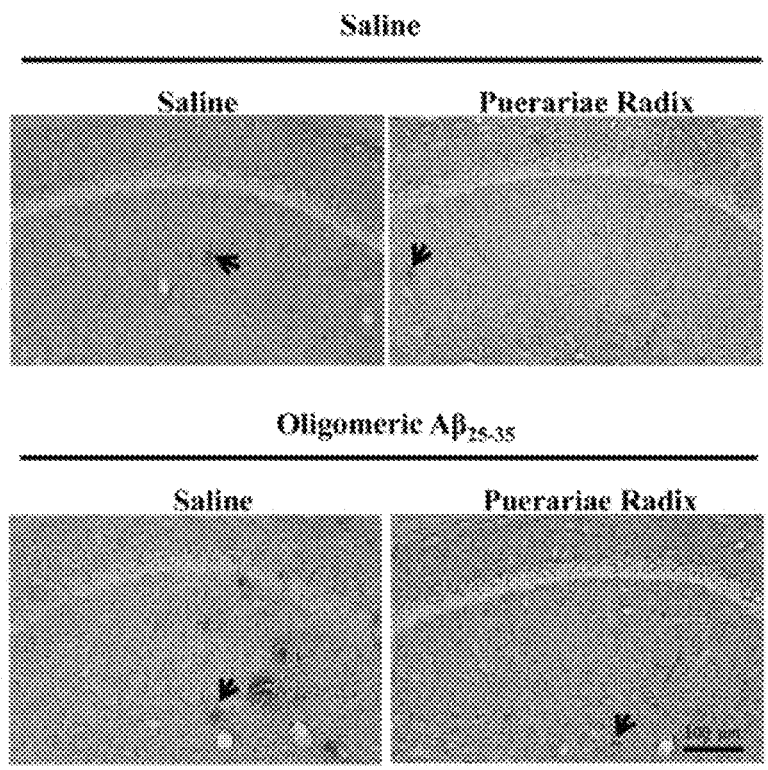
FIGS. 10A and 10B show the immunohistochemical staining results of Aβ accumulation in hippocampus CA1 region tissue slices.
Figure 10B:
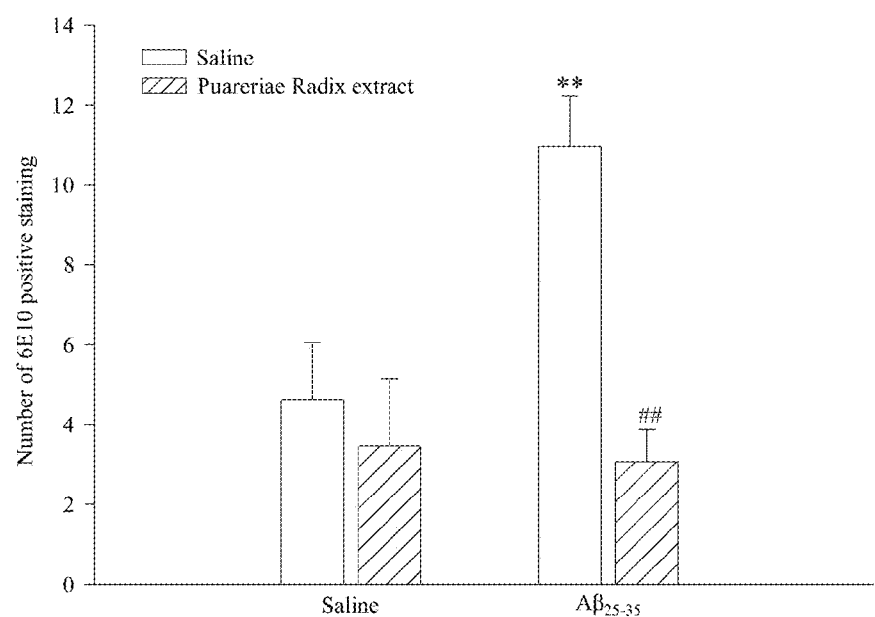
Figure 11A:
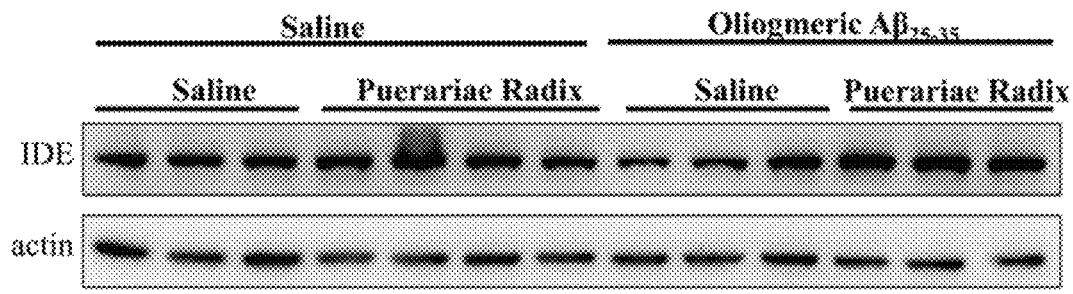
FIGS. 11A to 11F show the analysis results of the proteins related to the formation and removal of Aβ accumulation.
Figure 11B:
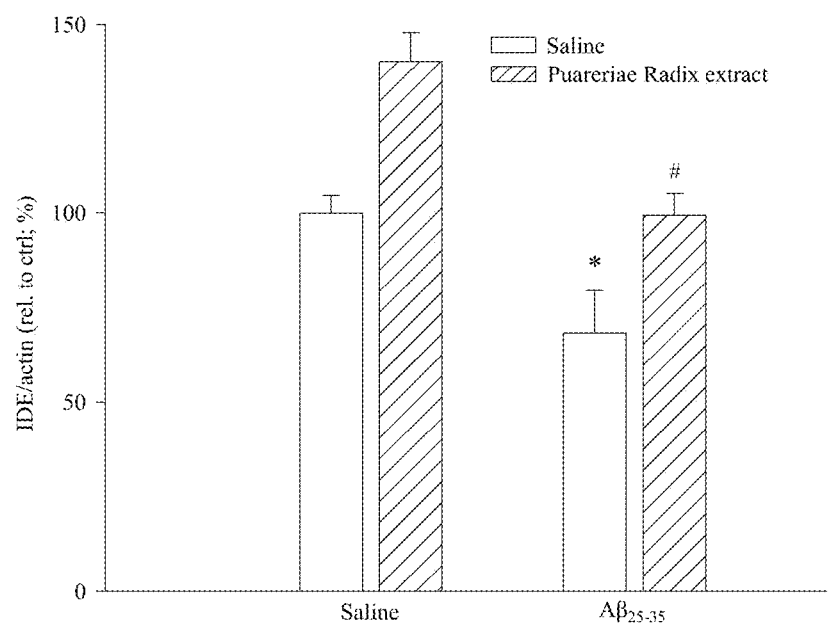
Figure 11C:
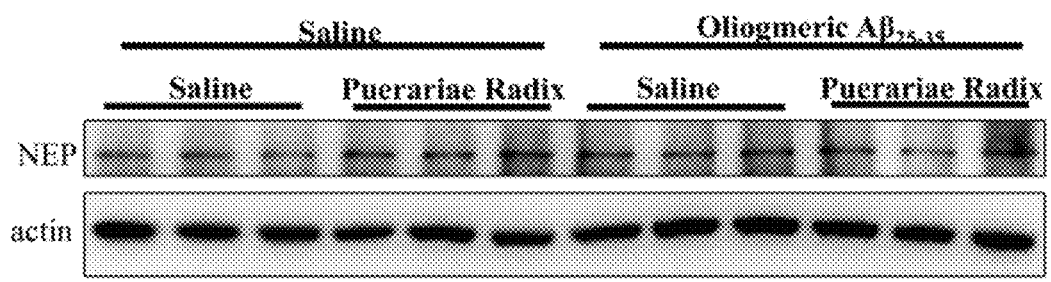
Figure 11D:
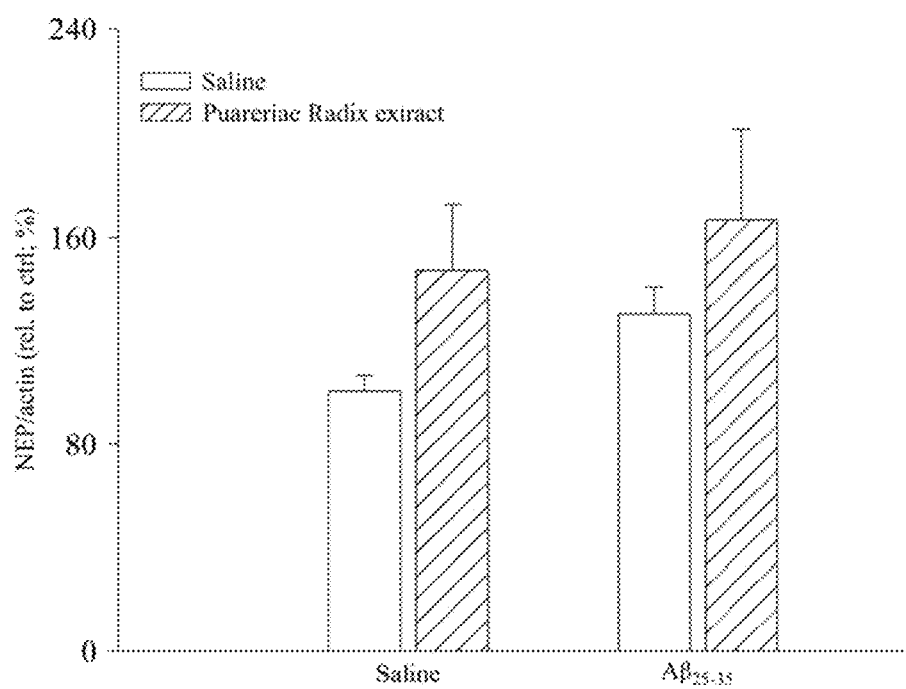
Figure 11E:
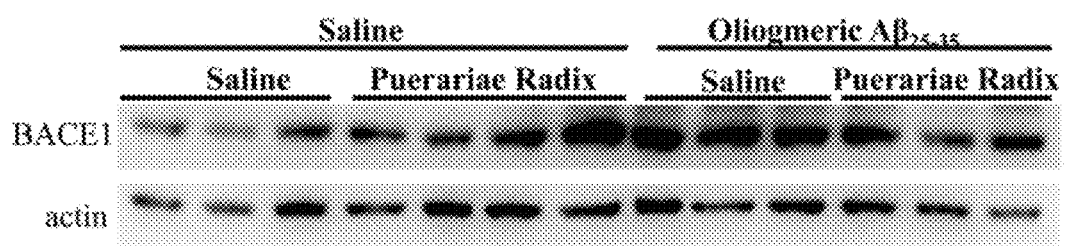
Figure 11F:
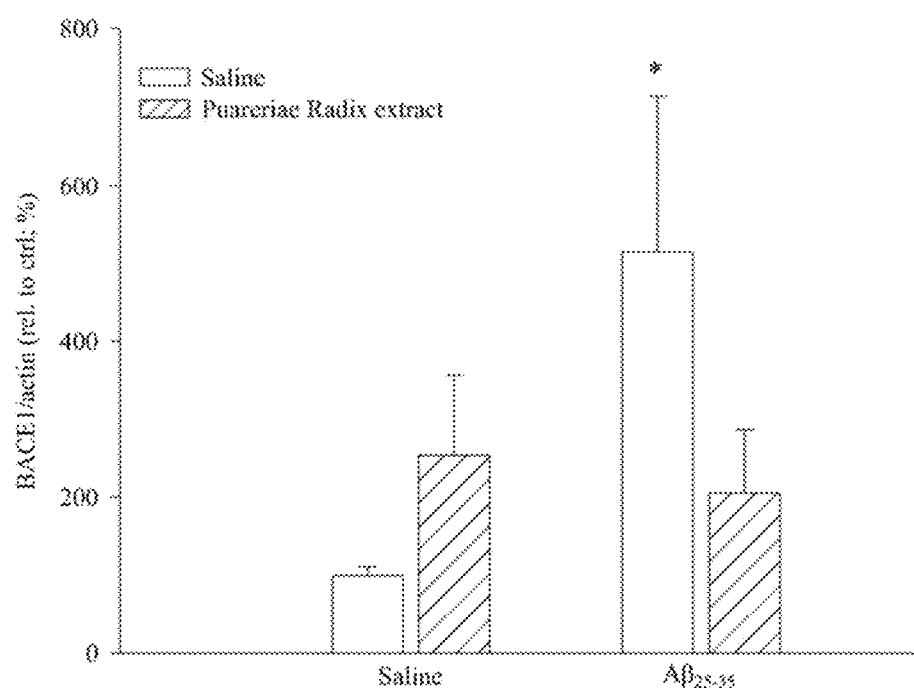

Further, the inventor has found that the Puerariae Radix extract can reduce the accumulation of Aβ. The inventor has analyzed the expression of 6E10 in hippocampus CA1 of the mice by tissue immunostaining so as to realize the accumulation situation of Aβ. The results show that the Aβ accumulation in the group injected with oligomeric $A\beta_{25-35}$ has significantly increased in comparison with the group injected with saline (FIGS. 10A and 10B); the signal of 6E10 is effectively reduced by pretreatment of the Puerariae Radix extract. The results show that the Puerariae Radix extract is able to relieve the Aβ accumulation caused by oligomeric $A\beta_{25-35}$ (FIGS. 10A and 10B). Furthermore, the expression of IDE protein (an enzyme which can digest Aβ) in hippocampus of the mice is analyzed by western blot analysis. The results show that the expression of IDE protein in the group injected with oligomeric $A\beta_{25-35}$ has significantly decreased in comparison with the group treated with saline (FIGS. 11A and 11B); whereas the expression of IDE protein in the group administrated with the Puerariae Radix extract has significantly increased in comparison with the group administrated with oligomeric $A\beta_{25-35}$ (FIGS. 11A and 11B). Similarly, the expression of NEP protein in hippocampus of the mice is also analyzed by western blot analysis. The results show that no matter whether groups are treated with oligomeric $A\beta_{25-35}$ or with the Puerariae Radix extract, there is no significant difference in the expression of NEP (FIGS. 11C and 11D). In addition, the expression of BACE1 in the group treated with oligomeric $A\beta_{25-35}$ is significantly higher than the group treated with saline (FIGS. 11E and 11F), indicating that oligomeric $A\beta_{25-35}$ causes the increase of β-secretase, which increases the chance of cutting APP in to Aβ. However, pretreating with the Puerariae Radix extract does not effectively reduce the expression of BACE1. Hence, the inventor speculates that the Puerariae Radix extract may improve the expression of IDE to achieve the result of reducing Aβ accumulation.

Figure 12A:
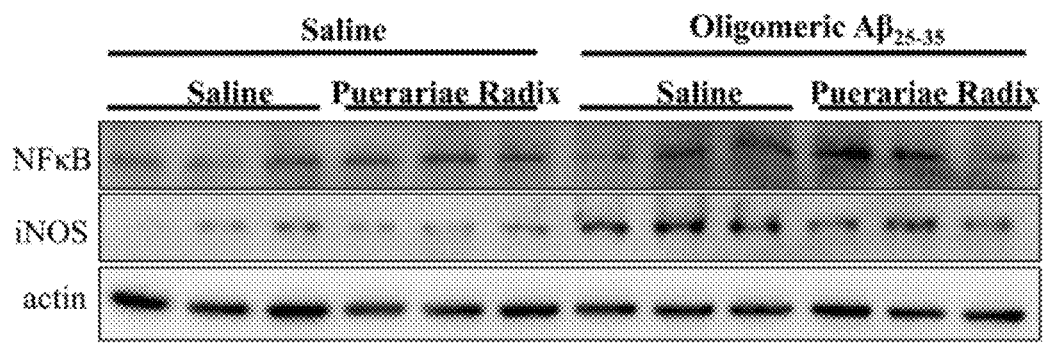
FIGS. 12A to 12C show the analysis results of the proteins related to inflammation.
Figure 12B:
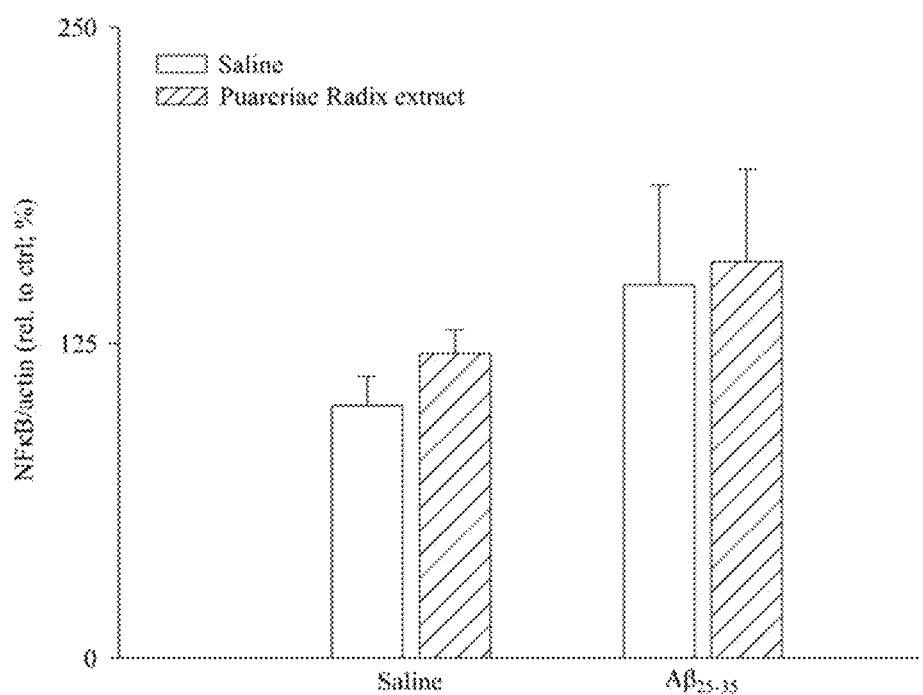
Figure 12C:
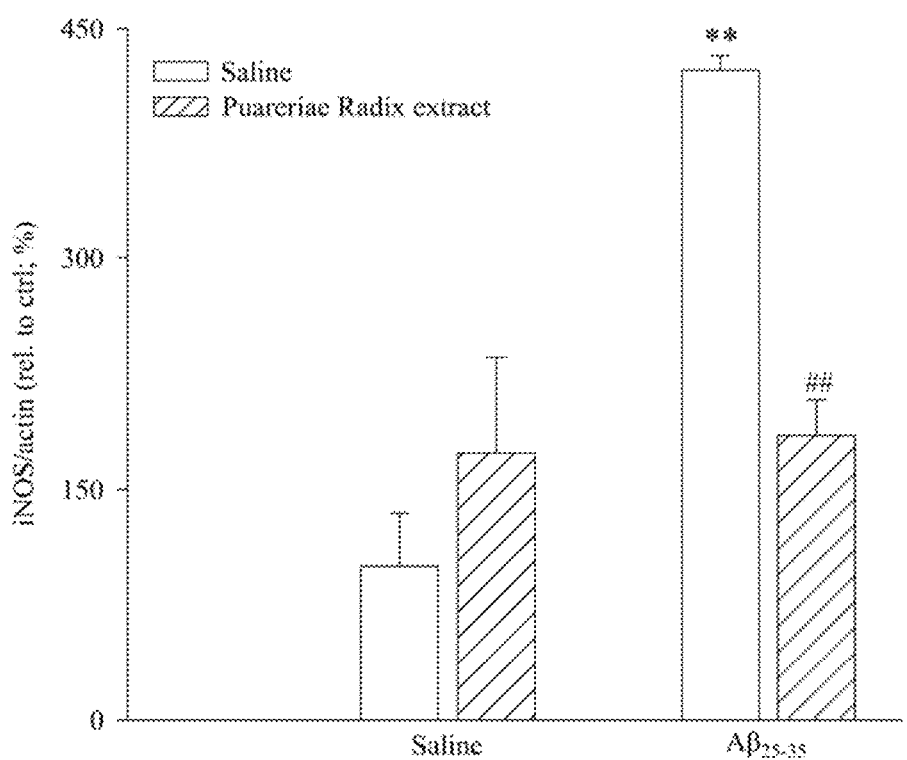
Figure 13A:
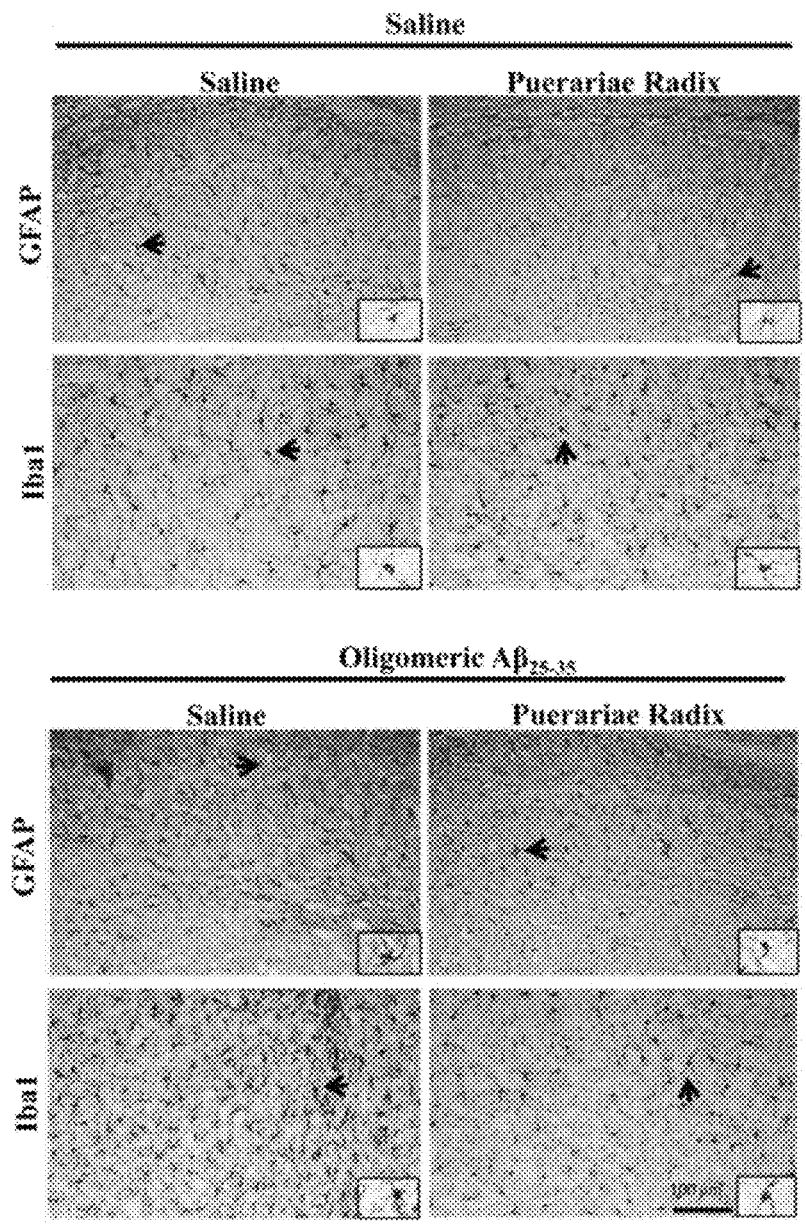
FIGS. 13A to 13C show the immunohistochemical staining results of the hippocampus glial cell.
Figure 13B:
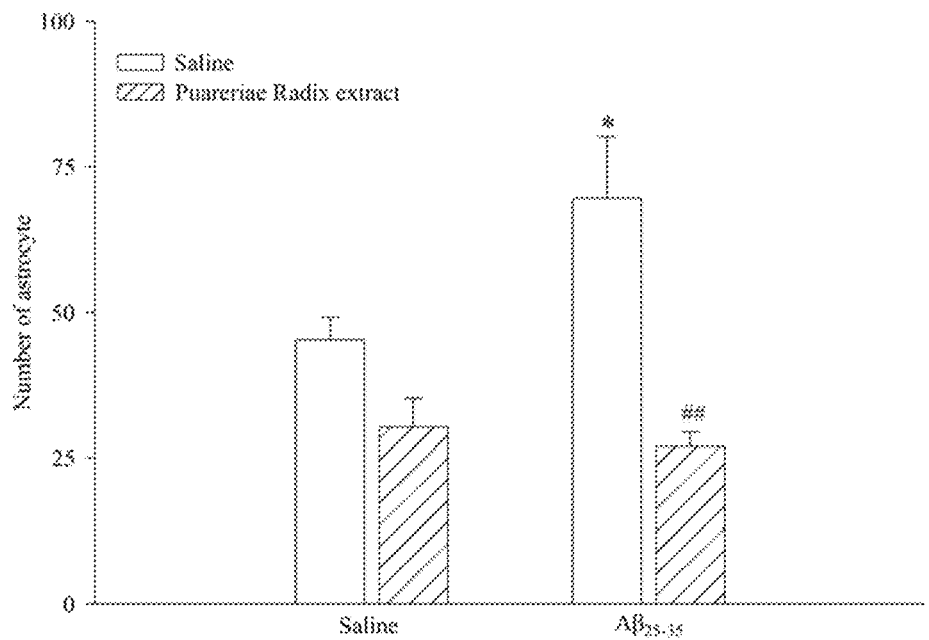
Figure 13C:
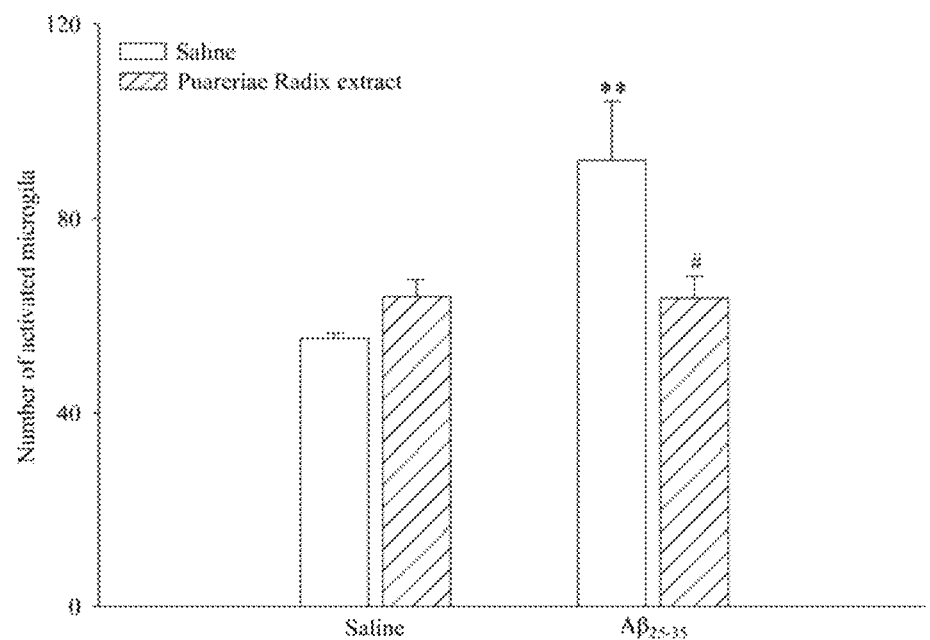
Figure 14A:
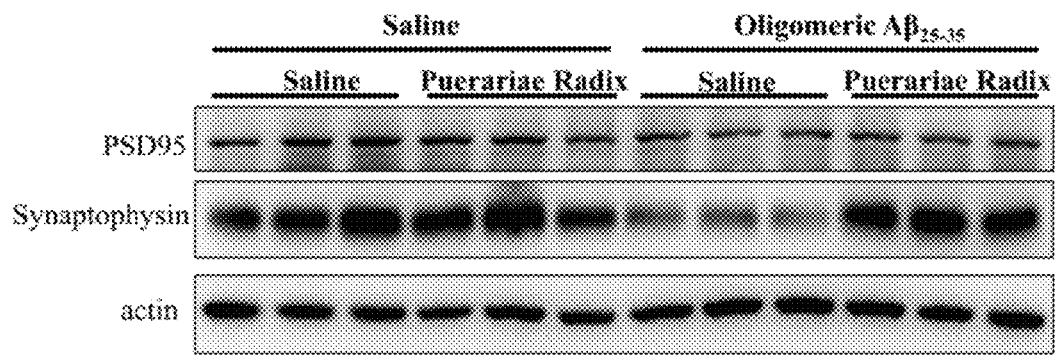
FIGS. 14A to 14C show the analysis results of the proteins related to synapse.
Figure 14B:
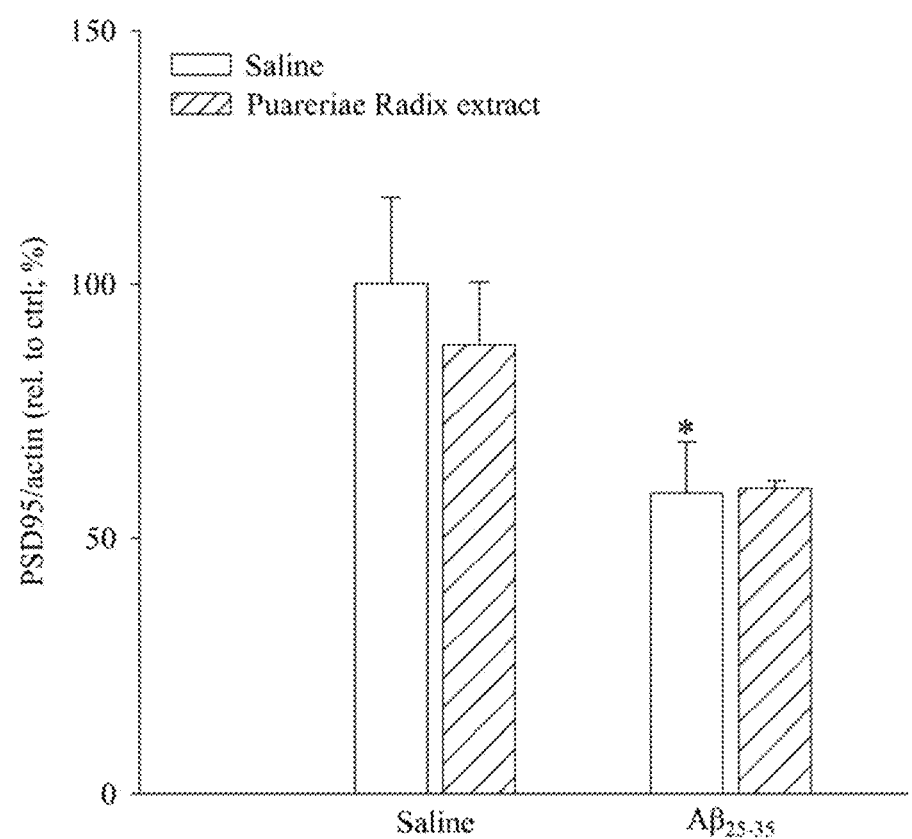
Figure 14C:
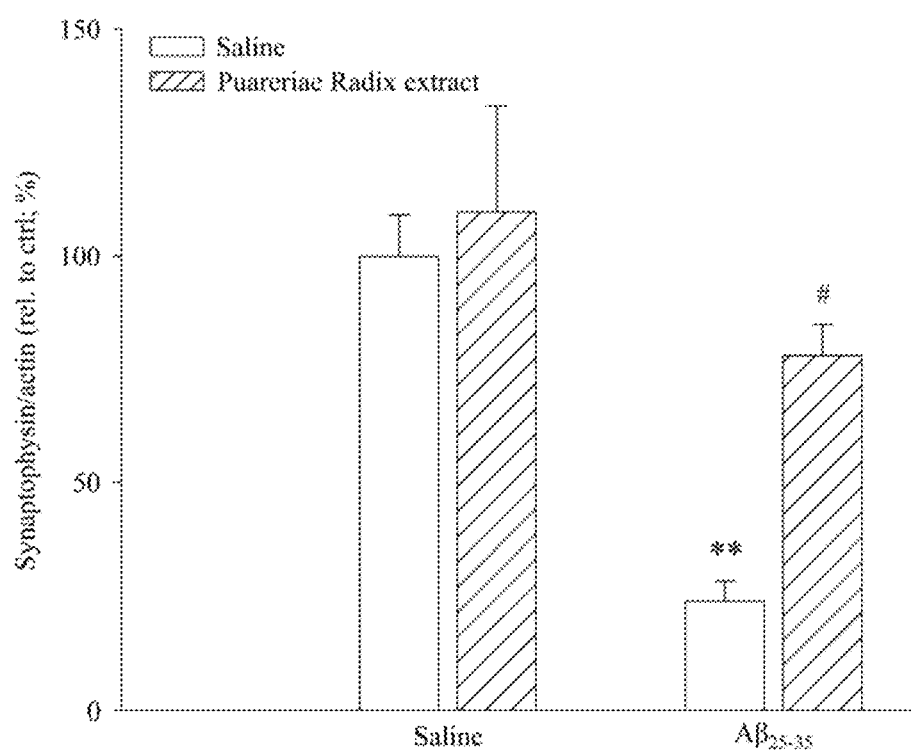

Further, the Puerariae Radix extract is able to prevent the inflammation induced by oligomeric $A\beta_{25-35}$. The inventor has analyzed the expression of the protein related to hippocampus inflammation by western blot. The inventor found that the expression of the nuclear factor kappa-light-chainenhancer of activated B cell (NFκB) in the group treated with oligomeric Aβ$_{25-35}$ is increased in comparison with the group treated with saline; whereas the pretreatment with the Puerariae Radix extract does not affect the expression of NFκB (FIGS. 12A and 12B). However, the expression of inducible nitric oxide synthase (iNOS) in the group treated with oligomeric Aβ$_{25-35}$ is significantly higher than the group treated with saline (FIGS. 12A and 12C). The pretreatment with the Puerariae Radix extract is able to effectively reduce the expression of iNOS (FIGS. 12A and 12C). Furthermore, the inflammation situation may be determined by analyzing the numbers of astrocyte and activated microglia (FIG. 13). The results show that the numbers of astrocyte and activated microglia in hippocampus CA1 injected with oligomeric Aβ$_{25-35}$ are significantly higher than the group injected with saline (FIGS. 13A to 13C); whereas the numbers of microglia and astrocyte treated with the Puerariae Radix extract are significantly lower in comparison with the group treated with saline. Such results show that the Puerariae Radix extract can prevent neuroinflammation caused by oligomeric Aβ$_{25-35}$ in hippocam pus CAL Likewise, the Puerariae Radix extract is able to provide relief from the decrease of synapse related proteins. The inventor has analyzed the expression of synapse related protein in mouse hippocampus via western blot (FIG. 14). The results show that the expression of postsynaptic density protein 95 (PSD95) in mice treated with oligomeric Aβ$_{25-35}$ is significant decreased in comparison that treated with saline (FIGS. 14A and 14B). However, the Puerariae Radix extract does not provide relief from the decrease in the expression of PSD95 caused by oligomeric Aβ$_{25-35}$. In addition, the expression of the presynaptic protein, synaptophysin, in the group treated with oligomer Aβ$_{25-35}$ is significant decreased in comparison with the group treated with saline (FIGS. 14A and 14C); whereas it significant rises again in the group pretreated with the Puerariae Radix extract (FIGS. 14A and 14C). Such results show that the Puerariae Radix extract is able to provide relief from the decrease in the number of synapse related proteins caused by oligomeric Aβ$_{25-35}$.

Figure 15A:
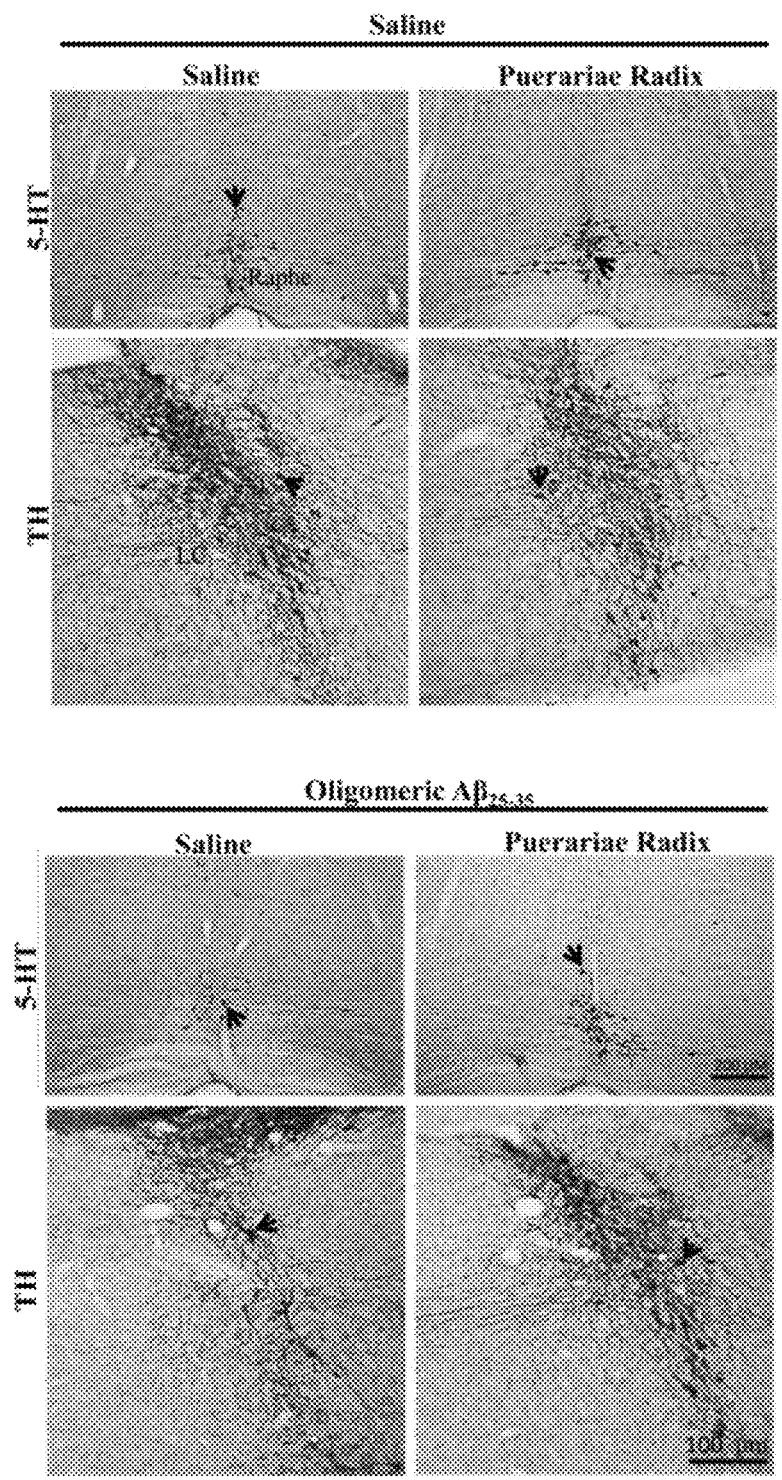
FIGS. 15A to 15C show the immunohistochemical analysis results of the noradrenergic neurons and serotonergic neurons tissue slices.
Figure 15B:
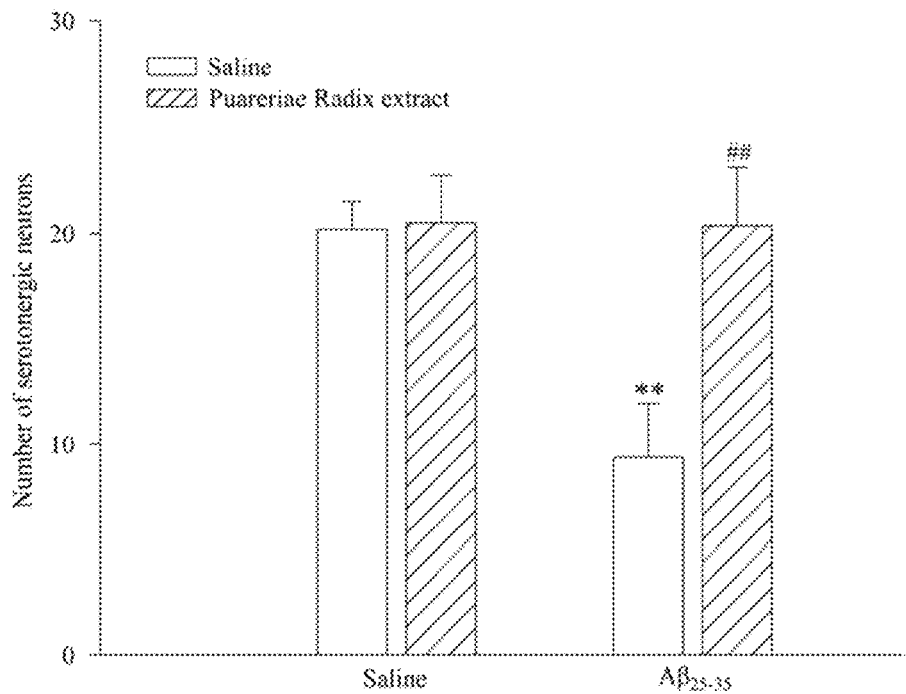
Figure 15C:
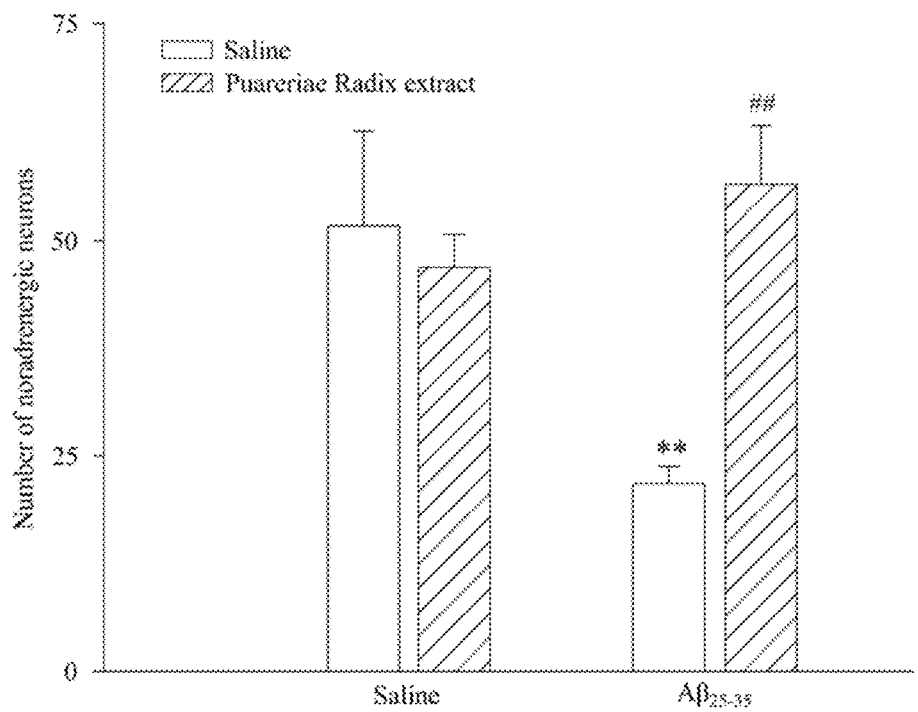
Figure 16:
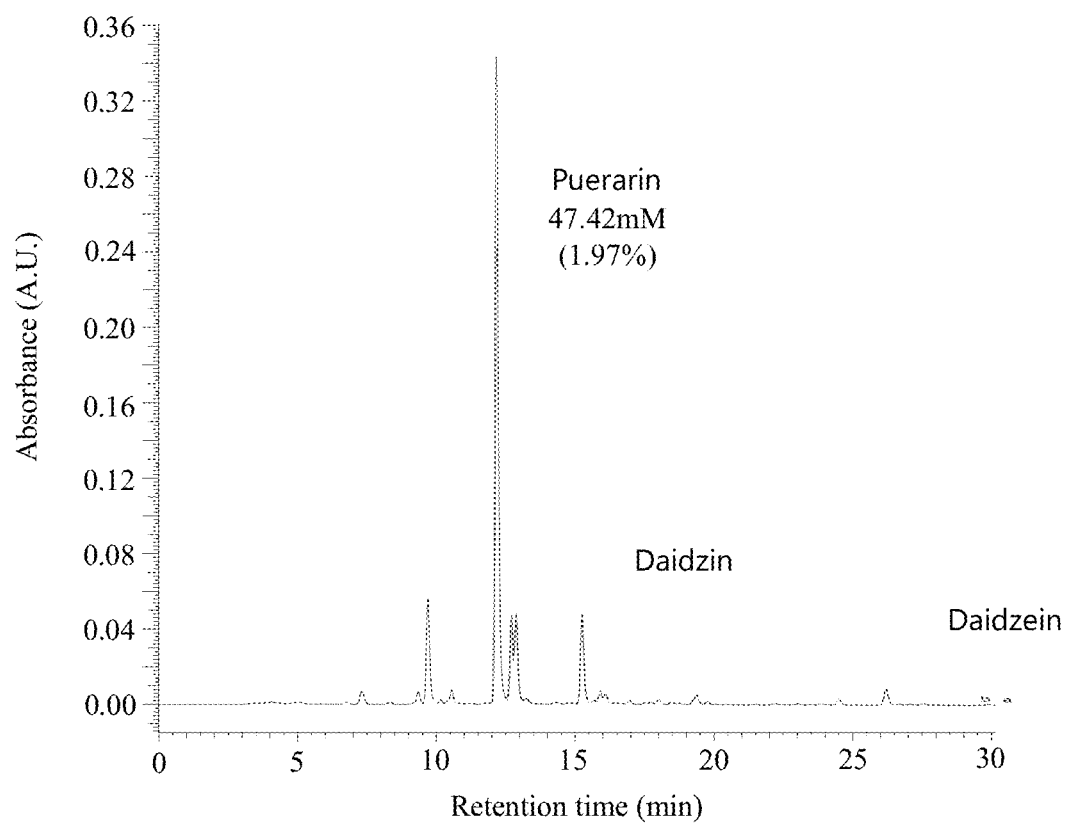
FIG. 16 shows the HPLC analysis result of the Puerariae Radix extract of the present invention, and shows the main components contained in the Puerariae Radix and the ratios thereof. The result is used to emphasize that the Puerariae Radix extract of the present invention containing many different components, including Puerarin.

Further, the Puerariae Radix extract can effectively provide relief from the damage in noradrenergic and serotonergic neurons caused by injected oligomeric Aβ$_{25-35}$ in hippocampus CAL The results are shown in FIG. 15, wherein the numbers of noradrenergic and serotonergic neurons in the group treated with oligomeric Aβ$_{25-35}$ are significantly less in comparison with the group treated with saline (FIGS. 15A to 15C); whereas the numbers of noradrenergic and serotonergic neurons in the group treated with the Puerariae Radix extract are significantly greater in comparison with the group treated with saline under the oligomeric Aβ$_{25-35}$ toxicity (FIGS. 15A to 15C).

Accordingly, the Puerariae Radix extract provided by the present invention has been determined that it is able to provide relief from the symptoms of anxiety and cognitive function disorder, and further possesses the function of protecting neurons, as shown in the in vitro and in vivo studies. It is an effect solution as a medication for memory dysfunction, and in improving learning ability and memory.

In summary, the invention disclosed herein has been described by means of exemplary embodiments and appended drawings. However, numerous modifications, variations and enhancements can be made thereto by those skilled in the art without changing the essential characteristics or technical spirit of the present invention. Therefore, it is to be understood that the present invention is not limited to the forms described in the exemplary embodiments and appended drawings, rather that the technical and protective scope of the present invention is defined by the following claims.

What is claimed is:

1. A method for relieving memory dysfunction using a Puerariae Radix extract, comprising:
    decocting a Puerariae Radix in water followed by concentrating the Puerariae Radix extract; and
    administrating an effective dose of the Puerariae Radix extract into a subject,
    wherein the Puerariae Radix extract comprises daidzein, daidzin and puerarin, and a ratio of daidzein, daidzin and puerarin is in a range of 1:1~30:50~100.

2. The method as in claim 1, wherein Chinese herbs decocted is limited to only the Puerariae Radix.

3. The method as in claim 1, wherein the effective dose is 1~1000 mg/kg.

4. The method as in claim 1, wherein the administrating further comprises administrating four times per day to once per week.

5. The method as in claim 1, wherein the administrating comprises administrating by means of an injection, orally, or topically.

6. The method as in claim 1, wherein the method further comprises functions of reducing β-amyloid accumulation, hyperphosphorylation of tau protein, and neuroinflammation, and increasing expression of synapse related proteins, a number of noradrenergic neurons, and a number of serotonergic neurons.

* * * * *